(12) United States Patent
Ishige et al.

(10) Patent No.: US 8,712,701 B2
(45) Date of Patent: Apr. 29, 2014

(54) POTENTIOMETRIC-SENSOR CHIP, POTENTIOMETRIC ASSAY, AND ASSAY KIT

(75) Inventors: Yu Ishige, Tokyo (JP); Masao Kamahori, Kokubunji (JP); Kuniaki Nagamine, Sendai (JP)

(73) Assignee: Hitachi, Ltd., Tokyo (JP)

( * ) Notice: Subject to any disclaimer, the term of this patent is extended or adjusted under 35 U.S.C. 154(b) by 348 days.

(21) Appl. No.: 13/126,766

(22) PCT Filed: Oct. 29, 2009

(86) PCT No.: PCT/JP2009/005748
§ 371 (c)(1),
(2), (4) Date: Jul. 22, 2011

(87) PCT Pub. No.: WO2010/052867
PCT Pub. Date: May 14, 2010

(65) Prior Publication Data
US 2011/0276278 A1    Nov. 10, 2011

(30) Foreign Application Priority Data

Nov. 4, 2008 (JP) .................... 2008-282689

(51) Int. Cl.
*G01N 27/00* (2006.01)
*G06F 19/00* (2011.01)
*G01N 27/327* (2006.01)
*G01N 33/66* (2006.01)
*G01N 33/49* (2006.01)

(52) U.S. Cl.
CPC ............ *G01N 27/3272* (2013.01); *G01N 33/66* (2013.01); *G01N 27/3277* (2013.01); *G01N 33/49* (2013.01)
USPC ....................... 702/25; 204/403.04; 205/780.5

(58) Field of Classification Search
CPC .......... G01N 27/3272; G01N 27/3277; G01N 33/66; G01N 33/49
USPC ........................ 702/19, 20, 22, 23, 25, 104; 204/403.04, 403.11, 411, 403.02; 435/14; 205/780.5
See application file for complete search history.

(56) References Cited

U.S. PATENT DOCUMENTS 7,955,484 B2 *  6/2011  Cai et al. .................. 204/403.04
2007/0131549 A1  6/2007  Cai et al.

FOREIGN PATENT DOCUMENTS

JP    02-245650    10/1990
JP    04-264246     9/1992

(Continued)

OTHER PUBLICATIONS

Katherine A. Erickson et al., Evaluation of a Novel Point-of-Care System, the i-STAT Portable Clinical Analyzer, Clinical Chemistry, 1993, pp. 283-287, vol. 39, No. 2.

*Primary Examiner* — John H Le
(74) *Attorney, Agent, or Firm* — Antonelli, Terry, Stout & Kraus, LLP.

(57) ABSTRACT

Provided is a potentiometric sensor chip in which the positional relationship among a reference electrode, a measurement electrode, and a sample inlet which enables measurement from the start of a reaction is defined, and further provided is a method for detecting the start time of the reaction. A very small amount of sample is measured with high accuracy. The very small quantity of sample is measured by a rate assay. When a reference electrode (103) is disposed between a sample inlet (102) and a measurement electrode (104), a sample solution arrives at the reference electrode (103) earlier than at the measurement electrode (104), whereby the surface potential of the measurement electrode (104) can be measured simultaneously when the sample solution arrives at the measurement electrode (104) and dissolves a reagent and thereby a reaction starts. The arrival of the sample solution at the measurement electrode (104) can be sensed by detecting the discontinuous change of the voltage observed by a voltmeter (106) at this time.

10 Claims, 17 Drawing Sheets

(56) References Cited

FOREIGN PATENT DOCUMENTS

| JP | 08-327587 | 12/1996 |
| JP | 9-500727 | 1/1997 |
| JP | 09-210955 | 8/1997 |
| JP | 2007-163499 | 6/2007 |
| WO | WO 2007/033079 A2 | 3/2007 |

* cited by examiner

FIG. 15
(a)
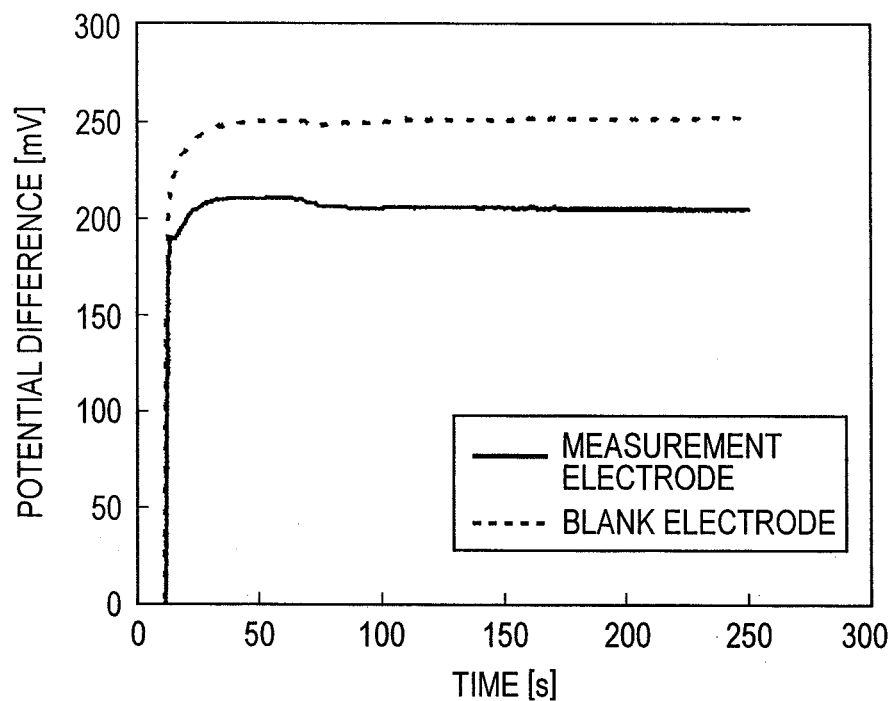
(b)
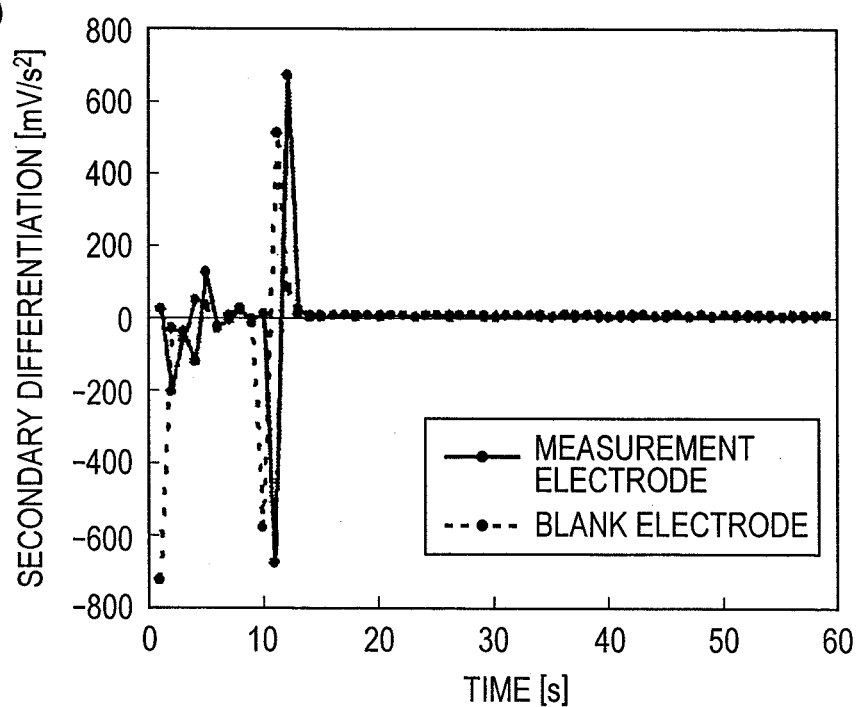

POTENTIOMETRIC-SENSOR CHIP, POTENTIOMETRIC ASSAY, AND ASSAY KIT

TECHNICAL FIELD

The present invention relates to a sensor, a measurement method and an assay kit which measure a biological material with high sensitivity by selectively inducing redox reaction of the biological material using an enzyme, etc and measuring the surface potential generated at that time.

BACKGROUND ART

In medical checkups, blood tests are widely conducted for the purpose of health condition check and early detection of an illness. In order to analyze many samples for many kinds of targets in test menu, samples are accumulated at a general hospital or testing laboratory where blood tests are conducted using a large clinical chemistry analyzer with a high throughput. Therefore, considering the time for transporting samples, waiting time for testing, time for making summary of testing and time for delivering summaries, usually it takes several days from sampling until testing results become available. In the case of medical checkups, in most cases this time lag does not matter since many people have a medical checkup every six months or once a year. However, in so-called point of care testing (POCT) where test results should be available on the site of sampling such as emergency tests including intraoperative tests, tests on ambulant patients, tests in ambulances, tests at clinics, and self-examinations at home including self-monitoring of blood glucose, the need for immediate availability of test results cannot be met if a clinical chemistry analyzer as mentioned above is used. In addition, since a clinical chemistry analyzer is expensive and must be operated by a specialist, it is not realistic to introduce a clinical chemistry analyzer at each site. The required device for POCT should be inexpensive enough for each site to afford to introduce, be compact enough to be carried to each site and be operable by a non-specialist user even though it may be not up to a clinical chemistry analyzer in terms of the number of targets in test menu and throughput.

The targets in test menu which the testing device for POCT is required to handle are as follows: sodium, potassium, and chloride as blood electrolytes which are measured in conventional blood tests, oxygen partial pressure, carbon dioxide partial pressure, creatinine, alkaline phosphatase, aspartate aminotransferase, alanine aminotransferase, urea nitrogen, lactase dehydrogenase (LD), gamma glutamyltransferase, cholesterol, bilirubin, choline esterase, neutral lipid, glucose, hematocrit and so on. The targets except electrolytes and hematocrit among them are usually measured using chemical reactions such as enzyme reactions. Measurement methods based on enzyme reactions which are used by currently commercially available testing devices for POCT are classified into a colorimetric reaction method and an amperometric assay (using enzyme electrodes). Since the colorimetric reaction method is also used in clinical chemistry analyzers, it is relatively easy to develop a POCT device which employs this measurement method. However, since an optics system is needed for colorimetric reactions, the size of a POCT device which can handle many kinds of targets should be a desk-top size or so. On the other hand, the amperometric assay is an electrical measurement method which does not require an optics system, so a device which adopts this method can be small or palm-sized even when it can measure many kinds of targets.

In the amperometric assay, three electrodes, which are a working electrode of gold or platinum, a counter electrode, and a reference electrode for keeping the working electrode potential constant, are placed in a solution in which an enzyme and redox compounds coexist. The working electrode, counter electrode, and reference electrode are connected to an amperometric device such as a potentiostat so as to enable measurement of current values which change when a voltage is applied between the working electrode and counter electrode. When a sample (for example, blood) containing a target analyte is added to the solution, the oxidization of target analyte is catalyzed by the enzyme and at the same time the redox compound in an oxidized state is brought into a reduced state. When a given voltage which can oxidize the redox compound is applied to the working electrode, the redox compound in a reduced state is oxidized on the working electrode, causing an electric current to flow in the working electrode. The oxidized redox compound reacts with the target analyte again by the enzyme catalysis and enters a reduced state. As this reaction is repeated, the oxidation reaction of the target analyte by the enzyme can be detected as an electric current. At this time, a redox compound with a sufficient concentration and a sufficiently large working electrode are needed so that a current value depending on the concentration of the target analyte is obtained, namely in the reaction system the target analyte concentration limits the reaction rate. Also, in order to minimize the voltage drop due to the electric resistance of the solution, it is desirable that the counter electrode and working electrode be as near to each other as possible. Furthermore, in order to simplify the constitution, one electrode which functions as both the reference electrode and counter electrode may be used and in that case, in order to minimize the voltage loss in the counter electrode, it is desirable that the counter electrode be as large as possible.

Since the sensitivity which is required for the glucose sensor for measuring the blood glucose level is not so high, the blood glucose level can be measured from a few drops of blood (for example, Patent Document 1). However, in a testing device for POCT which handles ordinary test menu, a larger volume of blood is required in order to maintain the sensitivity. For example, the i-Stat (Non-patent Document 1) developed as a testing device for POCT requires about 65 µl of blood. Although the required volume of blood can be decreased by decreasing the electrode area, in the amperometric assay, simply decreasing the electrode area leads to a decrease in signal (namely, current value), so there is difficulty in decreasing the electrode area.

A potentiometric assay is known as an electric measurement method in which signals do not depend on the electrode area. The potentiometric assay includes a measurement electrode (working electrode) made of gold or platinum and a reference electrode and an enzyme and a redox compound exist in a measuring solution (Patent Document 2). The measurement electrode and reference electrode are connected to a device which measures a voltage, such as a voltmeter. As a target analyte is added to a measuring solution, the target analyte is oxidized by enzyme reaction and at the same time the redox compound in an oxidized state is brought into a reduced state. The surface potential of the measurement electrode which is generated at that time is calculated in accordance with the Nernst Equation given below:

$$E = E^0 + \frac{RT}{nF} \ln(C_{ox}/C_{red}) \quad \text{[Equation 1]}$$

E: Surface potential of a measurement electrode
$E^0$: Standard potential of a redox compound R: Gas constant T: Absolute temperature n: Charge difference between the oxidized form and reduced form of the redox compound F: Faraday constant $C_{ox}$: Concentration of the oxidized form of the redox compound $C_{red}$: Concentration of the reduced form of the redox compound The above equation does not include the electrode area and the surface potential does not depend on the electrode area. Therefore, it is possible to decrease the electrode area without a decrease in signal intensity and reduce the required volume of sample. In addition, the distance between the reference electrode and measurement electrode does not pose the problem of voltage drop as seen in the amperometric assay and does not affect the measuring accuracy.

The amperometric assay and the potentiometric assay differ not only in the dependence of signals on the electrode area but also in whether signals depend on the reaction rate or reaction volume of enzyme reaction. Specifically, while signals proportional to the enzyme reaction rate are obtained in the amperometric assay, signals which depend on the volume of reduced substance (or oxidized substance) produced by enzyme reaction are obtained in the potentiometric assay. For this reason, while only the rate assay in which the reaction rate of enzyme reaction is measured can be used in the amperometric assay, the end point assay in which the total volume of reaction product is measured can be used in addition to the rate assay in the potentiometric assay. As a characteristic of an enzyme, its reaction rate is proportional to its concentration in a low substrate concentration range, but when the substrate concentration is high, the reaction rate is no longer proportional to the substrate concentration and when the concentration further goes up, the reaction rate becomes constant. This threshold concentration is called Michaelis constant and when the target analyte concentration in blood is not less than the Michaelis constant, the sample must be diluted for measurement in the rate assay, making measurement operation complicated. On the other hand, in the end point assay, since the total volume of reaction product is measured, there is no such a limitation and measurement can be made without dilution. One of enzymes of this type is cholesterol dehydrogenase and theoretically the potentiomeric assay may be said to be a method which can measure cholesterols without dilution.

RELATED ART DOCUMENT

Patent Documents

Patent Document 1: Japanese Patent Application Laid-Open Publication No. H2-245650

Patent Document 2: Japanese Patent Application Laid-Open Publication No. H9-500727

Non-Patent Document

Non-patent Document 1: Clin. Chemi. 39/2 (1993), p. 283-287

SUMMARY OF THE INVENTION

Problem to be Solved by the Invention

As a result of research and development of chip type enzyme sensors using the potentiometric assay having the abovementioned advantages, it has been found that although for accuracy improvement it is important to measure voltage change from the time of the start of enzyme reaction, the positional relations of the reference electrode and measurement electrode with respect to the sample inlet are not defined in the potentiometric enzyme sensor chip as described in Patent Document 2 and depending on the method of introducing a sample solution, measurement cannot be started from the time of the start of reaction. In addition, the method for detecting the start of chemical reaction and the method for detecting the introduction of a sample solution have not been known.

On the other hand, in the amperometric enzyme sensor chip, redox reaction on the measurement electrode as a result of application of voltage to the measurement electrode triggers the start of chemical reaction and thus there is no problem in the start of measurement at the time of start of reaction though there is a problem that measurement sensitivity depends on electrode area. Furthermore, the arrival of the sample solution at the measurement electrode is detected by detecting the point at which the current flowing to the measurement electrode becomes not zero.

The present invention provides a potentiometric enzyme sensor chip in which the positional relationship among a reference electrode, a measurement electrode, and a sample inlet is defined to enable measurement at the start of reaction and further provides a method for detecting the start time of the reaction. The invention makes it possible to make a measurement with high accuracy even with a very small amount of sample. By taking advantage of being able to detect the start time of a reaction, the invention makes it possible to use a rate assay to calculate the concentration of a target analyte even from a very small amount of sample.

Means for Solving the Problem

In the present invention, electrodes are disposed so that an introduced sample arrives at a reference electrode earlier than at a measurement electrode. The reference electrode is located between the sample inlet and the measurement electrode. The distance between the reference electrode and measurement electrode is larger than the width of each electrode. When a blank electrode is located in a non-branching flow channel, the blank electrode is located between the reference electrode and measurement electrode. When the blank electrode is located in a non-branching flow channel, both the distance between the reference electrode and the blank electrode and the distance between the blank electrode and the measurement electrode are larger than the width of each electrode. The flow channel is branched and the blank electrode and measurement electrode are located in branch flow channels respectively. When the blank electrode and measurement electrode are located in branch flow channels respectively, the sample is made to arrive at the reference electrode earlier by making the actual distance from the sample inlet to the reference electrode shorter than the actual distance from the sample inlet to the other electrodes or another approach. If plural measurement electrodes and plural blank electrodes are disposed, each measurement electrode and each blank electrode are located in different branch flow channels. The start of reaction is detected based on a discontinuous change in potential difference between the reference electrode and measurement electrode.

Effect of the Invention

According to the present invention, since the introduced sample arrives at the reference electrode earlier than at the measurement electrode, the solution introduced through the sample inlet touches the reference electrode and then the measurement electrode, so it is possible to start measurement at the time when the solution touches the measurement electrode. Since the distance between the reference electrode and measurement electrode is larger than the width of each electrode, the possibility that the order in which the solution touches the electrodes may be reversed is suppressed. When the blank electrode is located in a non-branching flow channel, it is disposed between the reference electrode and measurement electrode, so measurement of the potential of the blank electrode can be started at the time when the solution touches the blank electrode and crosstalk such as interfusion of an enzyme from the measurement electrode into the blank electrode is suppressed. When the blank electrode is located in a non-branching flow channel, by making the distance between the reference electrode and blank electrode larger than the width of each electrode, the possibility that the order in which the solution touches the electrodes may be reversed is suppressed. By branching the flow channel and disposing the blank electrode and measurement electrodes in different branch flow channels, crosstalk between the blank electrode and measurement electrode is suppressed. When the blank electrode and measurement electrode are located in different branch flow channels, the solution introduced through the sample inlet is made to touch the reference electrode before touching the blank electrode and measurement electrode by making the actual distance from the sample inlet to the reference electrode shorter than the actual distance from the sample inlet to the other electrodes, so at the time when the solution touches the blank electrode and measurement electrode, measurement of the potentials of these electrodes can be started. If plural measurement electrodes and plural blank electrodes are disposed, crosstalk between electrodes can be suppressed by disposing the measurement electrodes and the blank electrodes in different branch flow channels. The start of reaction is detected from a discontinuous change in potential difference between the reference electrode and measurement electrode, so the arrival of the solution at the measurement electrode and the start of reaction can be detected without the need for an additional electrode such as an electrode for detecting the solution. With these constitutions, the present invention has an effect that it is possible to measure concentrations highly accurately or make measurements by a rate assay even with a very small amount of sample.

BRIEF DESCRIPTION OF THE DRAWINGS

FIG. 15 is a view showing data obtained using a potentiometric enzyme sensor chip and a measurement device according to the present invention.

BEST MODE FOR CARRYING OUT THE INVENTION

Next, embodiments of the present invention will be described referring to drawings.

Figure 1:
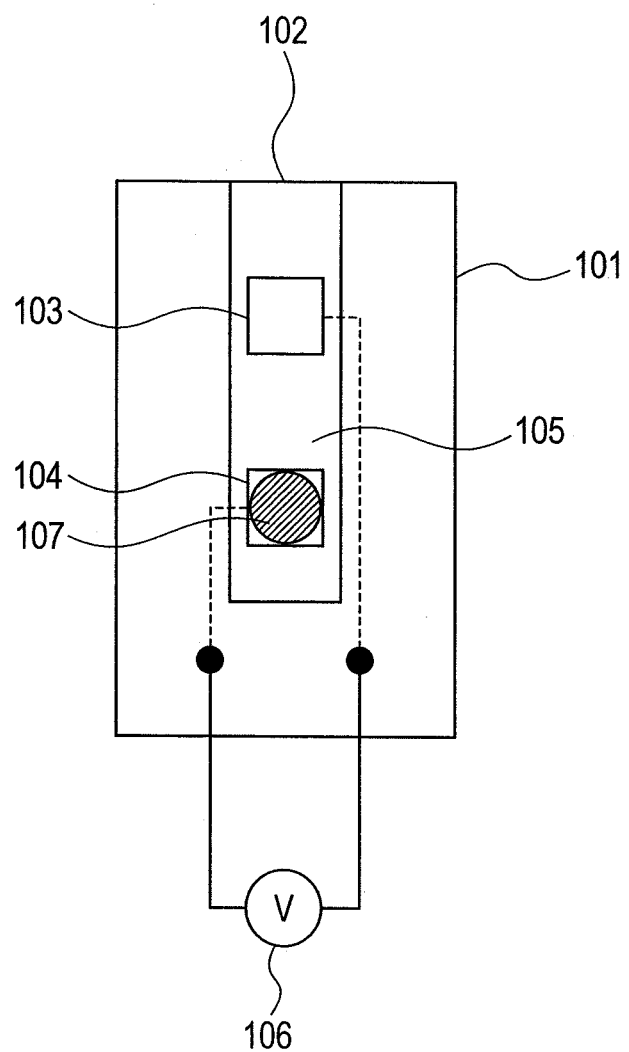
FIG. 1 is a view showing an example of a potentiometric enzyme sensor chip according to the present invention.

FIG. 1 shows an example of a potentiometric enzyme sensor chip according to the present invention. The chip has a substrate 101, a sample inlet 102, a reference electrode 103, a measurement electrode 104, and a flow channel 105 and the reference electrode 103 and measurement electrode 104 are connected to a voltmeter 106. The flow channel 105 may be hollow or filled with filter paper or a carrier such as gels or beads. In that case, when necessary, a sheet is attached to the substrate in a way to cover the flow channel. A silver silver-chloride electrode or the like is used for the reference electrode 103. A noble metal such as gold, silver or platinum is used for the measurement electrode 104. Preferably, an alkanethiol-modified gold electrode terminated with ferrocene such as 11-ferocenyl-1-undecanethiol is used. A reagent 107 is disposed over or around the measurement electrode 104 or in the surrounding carrier. Preferably the reagent is in a dry state.

Figure 2:
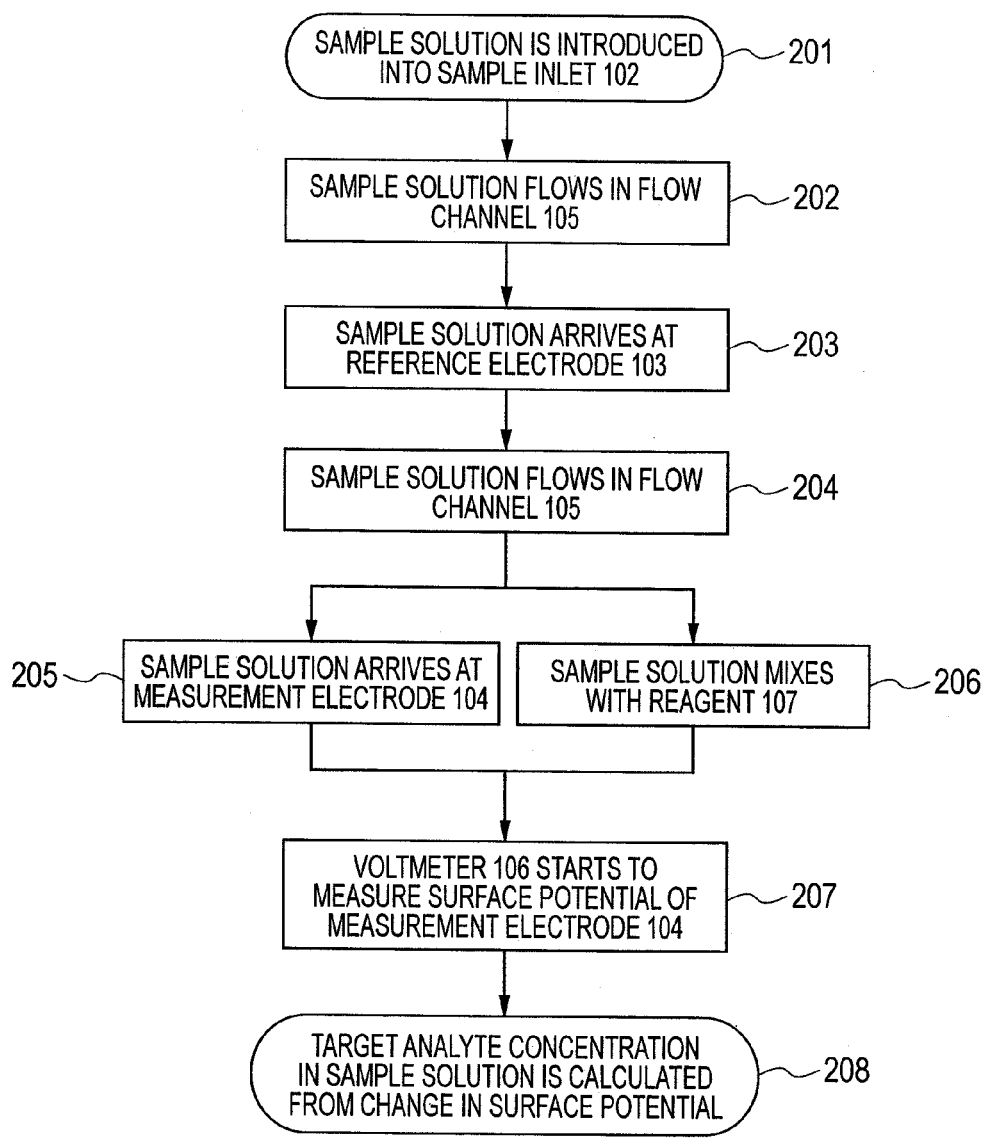
FIG. 2 is a view showing an example of a measurement flow using a potentiometric enzyme sensor chip according to the present invention.

Referring to the flowchart in FIG. 2, an example of measurement using the sensor chip shown in FIG. 1 is explained. First, a sample solution is introduced through the sample inlet 102 (201). The introduced sample solution flows in the flow channel 105 from top to bottom in the FIG. 202) and arrives at the reference electrode 103 (203).

At this time, for the sample solution to flow, any kind of driving force may be used, whether it is a capillary force, pressure or gravity force. The sample solution further flows in the flow channel 105 (204) and arrives at the measurement electrode 104 (205). Almost at the same time when the sample solution arrives at the measurement electrode 104, it dissolves the reagent 107 or mixes with the reagent 107 (206) and chemical reaction starts. Therefore, the start of reaction is almost simultaneous with the arrival of the sample solution at the measurement electrode 104. The change in the surface potential of the measurement electrode 104 as caused by this chemical reaction is measured by the voltmeter 106 as a change in the potential difference between the reference electrode 103 and measurement electrode 104 (207). It is not until the sample solution arrives at both the reference electrode 103 and measurement electrode 104 that the surface potential of the measurement electrode 104 can be measured by the voltmeter 106. Therefore, in the sensor chip shown in FIG. 1, the time when measurement of the surface potential of the measurement electrode 104 becomes possible is almost the same as the time when reaction starts, so the surface potential of the measurement electrode 104 can be measured from the start of chemical reaction. On the other hand, if the positions of the reference electrode 103 and measurement electrode 104 are reverse, the sample solution arrives at the measurement electrode before arriving at the reference electrode. Although chemical reaction starts upon the arrival of the sample solution at the measurement electrode 104, it is after the sample solution arrives at the reference electrode that it becomes possible to measure the surface potential of the measurement electrode, so it is impossible to measure the surface potential of the measurement electrode from the start of reaction. Therefore, the positional relationship between the electrodes as shown in FIG. 1 is desirable. Also in order to ensure that the sample solution spreads all over the surface of the reference electrode 103 before touching the measurement electrode 104, it is desirable that the distance between the reference electrode 103 and measurement electrode 104 be larger than the size of the reference electrode 103. The target analyte concentration in the sample solution is calculated using the measured change in surface potential (208). In the method for calculating the target analyte concentration, it is also possible to employ a rate assay or fitting for the reaction process, taking advantage of being able to not only obtain the absolute value of surface potential but also detect the start of reaction. As the voltmeter 106, a field-effect transistor (FET) may be used.

Figure 3:
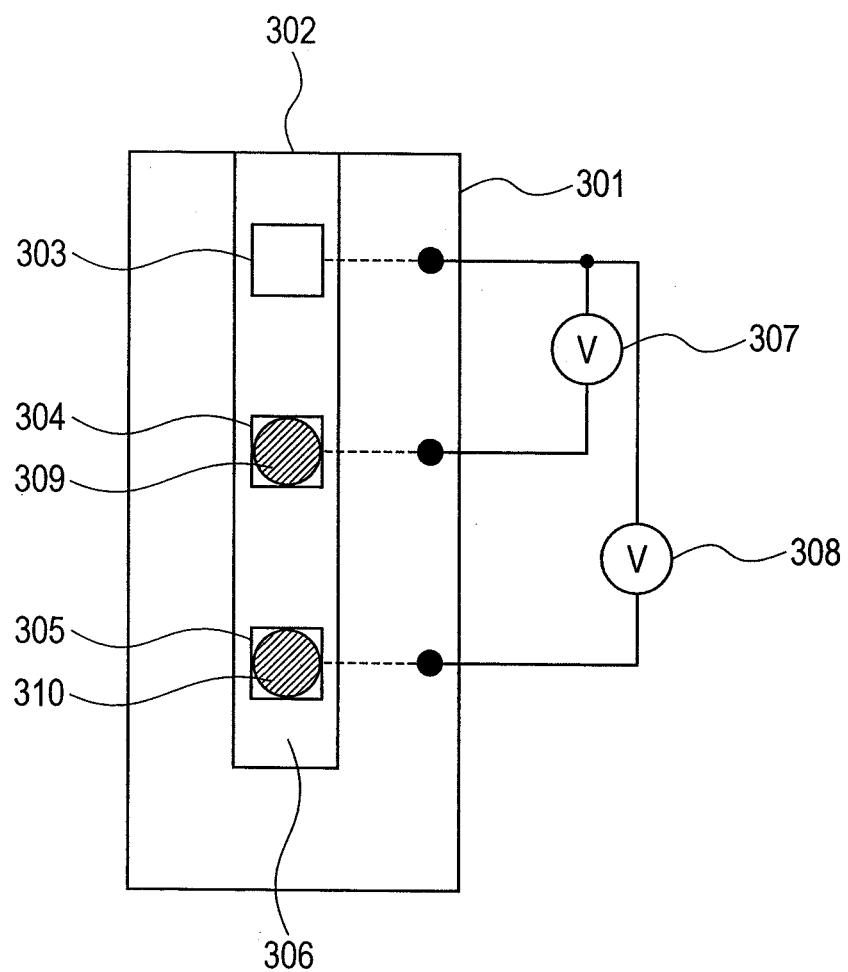
FIG. 3 is a view showing an example of a potentiometric enzyme sensor chip according to the present invention.

FIG. 3 shows an example of a potentiometric enzyme sensor chip according to the present invention. The chip has a substrate 301, a sample inlet 302, a reference electrode 303, a blank electrode 304, a measurement electrode 305, and a flow channel 306 and the reference electrode 303 and blank electrode 304 are connected to a voltmeter 307 and the reference electrode 303 and the measurement electrode 305 are connected to a voltmeter 308. The flow channel 306 may be hollow or filled with filter paper or a carrier such as gels or beads. In that case, when necessary, a sheet is attached to the substrate in a way to cover the flow channel. A silver silver-chloride electrode or the like is used for the reference electrode 303. A noble metal such as gold, silver or platinum is used for the blank electrode 304 and measurement electrode 305. Preferably, an alkanethiol-modified gold electrode terminated with ferrocene such as 11-ferocenyl-1-undecanethiol is used. Reagents 309 and 310 are disposed over or around the blank electrode 304 and measurement electrode 305 or in the surrounding carrier. Preferably the reagents 309 and 310 are in a dry state. The reagent 309 for the blank electrode 304 does not contain some of the enzymes and catalysts as contained in the reagent 310 for the measurement electrode 305 or contains none of them. Therefore, the influence of potential variation of the reference electrode 303 or an interfering substance in the sample can be eliminated by comparison in surface potential between the blank electrode 304 and the measurement electrode 305.

Figure 4:
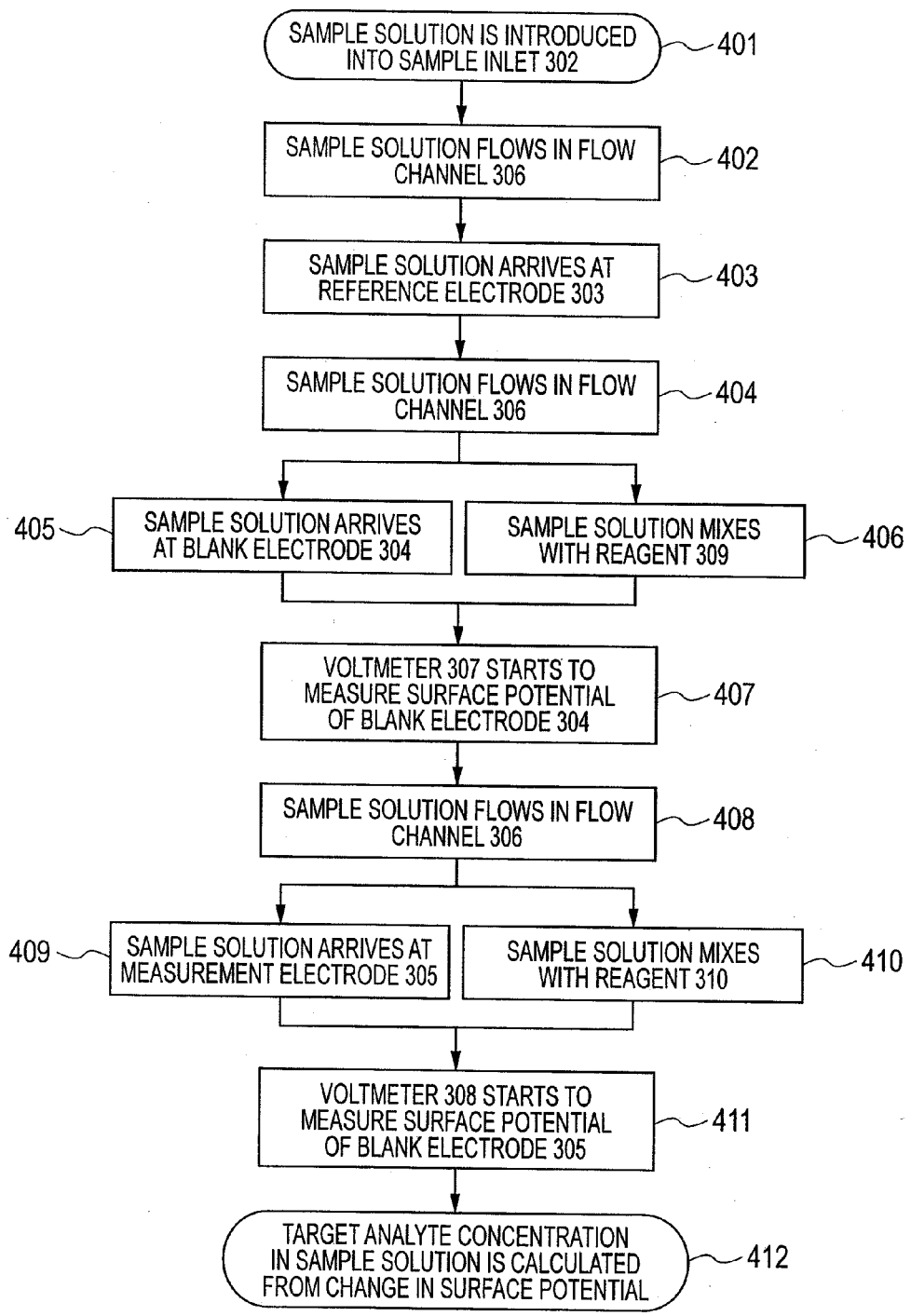
FIG. 4 is a view showing an example of a measurement flow using a potentiometric enzyme sensor chip according to the present invention.

Referring to the flowchart in FIG. 4, an example of measurement using the sensor chip shown in FIG. 3 is explained. First, a sample solution is introduced through the sample inlet 302 (401). The introduced sample solution flows in the flow channel 306 from top to bottom in the FIG. 402) and arrives at the reference electrode 303 (403).

At this time, for the sample solution to flow, any kind of driving force may be used, whether it is a capillary force, pressure or gravity force. The sample solution further flows in the flow channel 306 (404) and arrives at the blank electrode 104 (405). Almost at the same time when the sample solution arrives at the blank electrode 304, it dissolves the reagent 309 for the blank electrode 304 or mixes with the reagent 309 (406) and chemical reaction starts. The sample solution further flows in the flow channel 306 (408) and arrives at the measurement electrode 305 (409) and also dissolves the reagent 310 for the measurement electrode 305 or mixes with the reagent 310 (410) and chemical reaction starts. Therefore, the arrival of the sample solution at the blank electrode 304 is almost simultaneous with the reaction between the reagent 309 for the blank electrode 304 and the sample solution, and the arrival of the sample solution at the measurement electrode 305 is almost simultaneous with the reaction between the reagent 310 for the measurement electrode 305 and the sample solution. The changes in the surface potentials of the blank electrode 304 and measurement electrode 305 as caused by these chemical reactions are measured by the voltmeter 307 and voltmeter 308 as changes in potential difference between the reference electrode 303 and blank electrode 304 and between the reference electrode 303 and measurement electrode 305 respectively (407, 411). As in the case of FIG. 1, at the blank electrode 304 and measurement electrode 305, when their respective chemical reactions start, it becomes possible to measure their respective surface potentials. Here, as the sample solution flows, interfusion of part of the reagent 309 for the blank electrode 304 onto the measurement electrode 305 may occur. However, since usually the components contained in the reagent 309 for the blank electrode 304 are also contained in the reagent 310 for the measurement electrode 305, it is not a serious problem. However, if the positions of the blank electrode 304 and measurement electrode 305 are reverse, interfusion of part of the reagent 310 for the measurement electrode onto the blank electrode may occur. If it happens, a potential change depending on the target analyte would occur on the blank electrode as well, posing a serious problem for measurement. Therefore, the positional relationship among the electrodes as shown in FIG. 3 is desirable. Also, in order to ensure that the sample solution spreads all over the surface of the reference electrode 303 before touching the blank electrode 304, it is desirable that the distance between the reference electrode 303 and blank electrode 304 be larger than the size of the reference electrode 303. The target analyte concentration in the sample solution is calculated using the measured changes in surface potential (412). In the method for calculating the target analyte concentration, it is also possible to employ a rate assay or fitting for the reaction process, taking advantage of being able to not only obtain the absolute value of surface potential of the measurement electrode and the surface potential difference between the measurement electrode and blank electrode but also detect the start of reaction. As the voltmeters 307 and 308, field-effect transistors (FETs) may be used.

Figure 5:
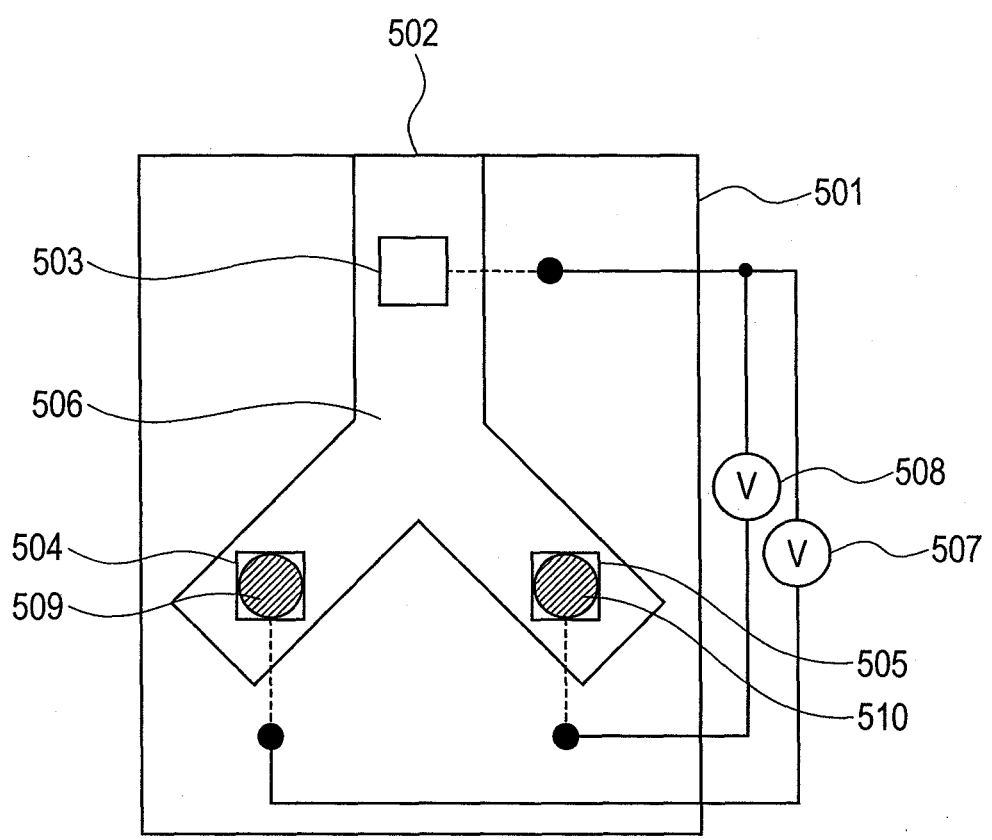
FIG. 5 is a view showing an example of a potentiometric enzyme sensor chip according to the present invention.

FIG. 5 shows an example of a potentiometric enzyme sensor chip according to the present invention. The chip has a substrate 501, a sample inlet 502, a reference electrode 503, a blank electrode 504, a measurement electrode 505, and a flow channel 506 and the reference electrode 503 and blank electrode 504 are connected to a voltmeter 507 and the reference electrode 503 and measurement electrode 505 are connected to a voltmeter 508. The flow channel 505 may be hollow or filled with filter paper or a carrier such as gels or beads. In that case, when necessary, a sheet is attached to the substrate in a way to cover the flow channel. A silver silver-chloride electrode or the like is used for the reference electrode 503. A noble metal such as gold, silver or platinum is used for the blank electrode 504 and measurement electrode 505. Preferably, an alkanethiol-modified gold electrode terminated with ferrocene such as 11-ferocenyl-1-undecanethiol is used. Reagents 509 and 510 are disposed over or around the blank electrode 504 and measurement electrode 505 or in the surrounding carrier. Preferably the reagents 509 and 510 are in a dry state. The reagent 509 for the blank electrode 504 does not contain some of the enzymes and catalysts as contained in the reagent 510 for the measurement electrode 505 or contains none of them. Therefore, the influence of potential variation of the reference electrode 503 or an interfering substance in the sample can be eliminated by comparison in surface potential between the blank electrode 504 and measurement electrode 505.

Figure 6:
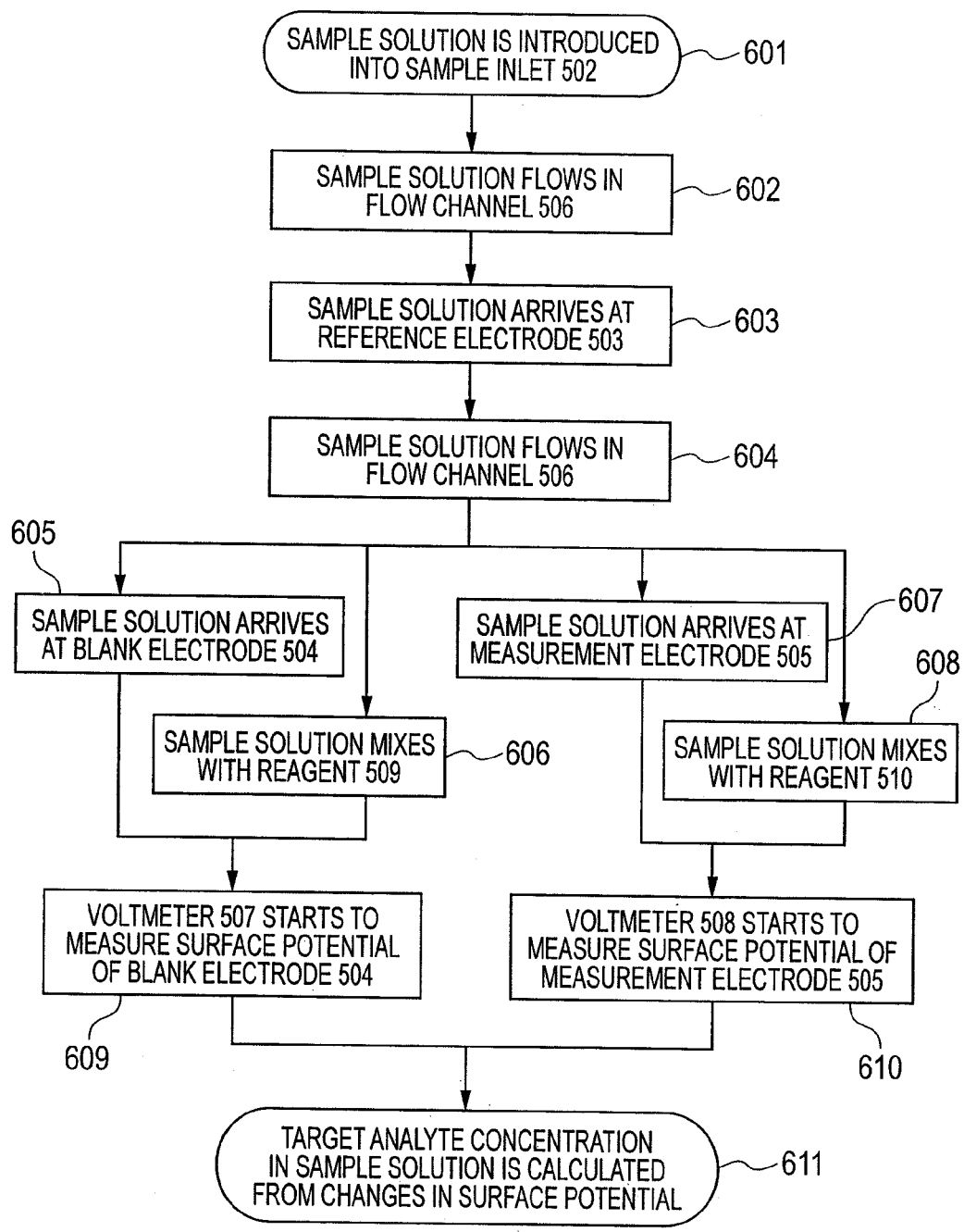
FIG. 6 is a view showing an example of a measurement flow using a potentiometric enzyme sensor chip according to the present invention.

Referring to the flowchart in FIG. 6, an example of measurement using the sensor chip shown in FIG. 5 is explained. First, a sample solution is introduced through the sample inlet 502 (601). The introduced sample solution flows in the flow channel 506 from top to bottom in the FIG. 602) and arrives at the reference electrode 503 (603). At this time, for the sample solution to flow, any kind of driving force may be used, whether it is a capillary force, pressure or gravity force. The sample solution further flows in the flow channel 506 (604) and arrives at the blank electrode 504 and measurement electrode 505 (605, 607) through a branching point. Almost at the same time when the sample solution arrives at the blank electrode 504, it dissolves the reagent 509 for the blank electrode 504 or mixes with the reagent 509 (606) and chemical reaction starts. Also, almost at the same time when the sample solution arrives at the measurement electrode 505, it dissolves the reagent 510 for the measurement electrode 505 or mixes with the reagent 510 (608) and chemical reaction starts. Therefore, the arrival of the sample solution at the blank electrode 504 is almost simultaneous with the reaction between the reagent 509 for the blank electrode 504 and the sample solution, and the arrival of the sample solution at the measurement electrode 505 is almost simultaneous with the reaction between the reagent 510 for the measurement electrode 505 and the sample solution. The changes in the surface potentials of the blank electrode 504 and measurement electrode 505 as caused by these chemical reactions are measured by the voltmeter 507 and voltmeter 508 as changes in potential difference between the reference electrode 503 and blank electrode 504 and between the reference electrode 503 and measurement electrode 505 respectively (609, 610). As in the case of FIG. 1, at the blank electrode 504 and measurement electrode 505, when their respective chemical reactions start, it becomes possible to measure their respective surface potentials. Here, since the blank electrode 504 and measurement electrode 505 are located in different branch flow channels, there does not exist the problem of crosstalk between the blank electrode and measurement electrode which may arise in the sensor chip shown in FIG. 2. Also, in order to ensure that the sample solution spreads all over the surface of the reference electrode 503 before touching the blank electrode 504 and measurement electrode 505, it is desirable that the distance between the reference electrode 503 and blank electrode 504 and the distance between the reference electrode 503 and measurement electrode 505 be larger than the size of the reference electrode 503. The target analyte concentration in the sample solution is calculated using the measured changes in surface potential (611). In the method for calculating the target analyte concentration, it is possible to employ a rate assay or fitting for the reaction process, taking advantage of being able to not only obtain the absolute value of surface potential of the measurement electrode and the surface potential difference between the measurement electrode and blank electrode but also detect the start of reaction. Instead of the voltmeters 507 and 508, field-effect transistors (FETs) may be used.

Figure 7:
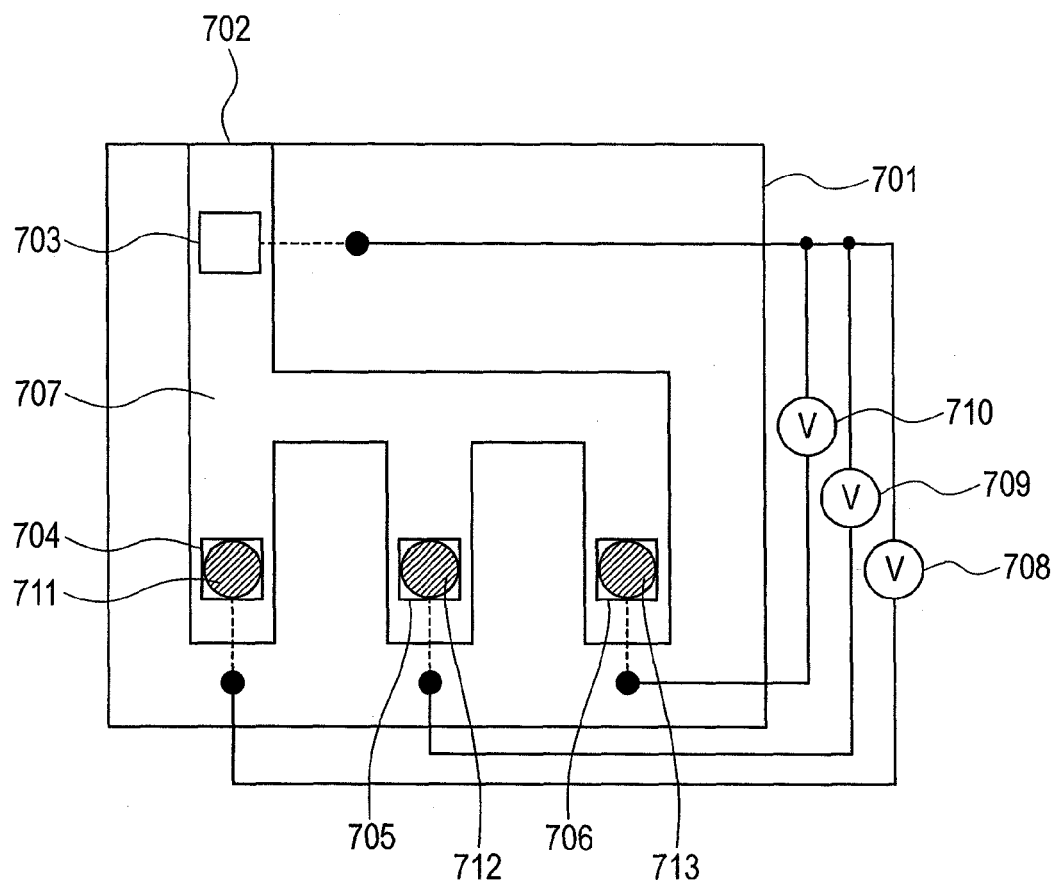
FIG. 7 is a view showing an example of a potentiometric enzyme sensor chip according to the present invention.

FIG. 7 shows an example of a potentiometric enzyme sensor chip according to the present invention. The chip has a substrate 701, a sample inlet 702, a reference electrode 703, a blank electrode 704, a measurement electrode A 705, a measurement electrode B 706, and a flow channel 707 and the reference electrode 703 and blank electrode 704 are connected to a voltmeter 708 and the reference electrode 703 and measurement electrode A 705 are connected to a voltmeter 709, and the reference electrode 703 and measurement electrode B 706 are connected to a voltmeter 710. The flow channel 707 may be hollow or filled with filter paper or a carrier such as gels or beads. In that case, when necessary, a sheet is attached to the substrate in a way to cover the flow channel. A silver silver-chloride electrode or the like is used for the reference electrode 703. A noble metal such as gold, silver or platinum is used for the blank electrode 704, measurement electrode A 705 and measurement electrode B 706. Preferably, an alkanethiol-modified gold electrode terminated with ferrocene such as 11-ferocenyl-1-undecanethiol is used. Reagents 711, 712, and 713 are disposed over or around the blank electrode 704, measurement electrode A 705 and measurement electrode B 706 or in the surrounding carrier. Preferably the reagents 711, 712, and 713 are in a dry state. The reagent 711 for the blank electrode 704 does not contain some of the enzymes and catalysts as contained in the reagent 712 for the measurement electrode A 705 and the reagent 713 for the measurement electrode B 706 or contains none of them. Therefore, the influence of potential variation of the reference electrode 703 or an interfering substance in the sample can be eliminated by comparison in surface potential between the blank electrode 704 and measurement electrode A 705 or measurement electrode B 706. Examples of the reagents 711, 712, and 713 are listed below.

Reagent 711: 299 μmol/l potassium ferricyanide, 1 μmol/l potassium ferrocyanide, and 0.1 M potassium phosphate (pH 7); 1 μl dropped and dried. Reagent 712: 299 μmol/l potassium ferricyanide, 1 μmol/l potassium ferrocyanide, 0.1 M potassium phosphate (pH 7), and 10 mg/ml glucose dehydrogenase; 1 μl dropped and dried. Reagent 713: 299 μmol/l potassium ferricyanide, 1 μmol/l potassium ferrocyanide, 0.1 M Tris-HCl (pH 8.5), 10 mg/ml cholesterol esterase and 10 mg/ml cholesterol dehydrogenase; 1 μl dropped and dried. The enzymes contained in the reagents 712 and 713 vary depending on target analyte as shown in Table 1. At the same time, the type of buffer, the concentration of potassium ferricyanide, and the concentration of potassium ferrocyanide are changed as appropriate.

TABLE 1

| Target analyte | Enzyme |
| --- | --- |
| Glucose | Glucose dehydrogenase |
| Cholesterol | Cholesterol esterase |
|  | Cholesterol dehydrogenase |
| Lactic acid | Lactic acid dehydrogenase |
| Pyruvic acid | Pyruvic acid dehydrogenase |

TABLE 1-continued

| Target analyte | Enzyme |
|---|---|
| Alcohol | Alcohol dehydrogenase |
| Neutral lipid | Lipase, glycerol dehydrogenase |

Figure 8:
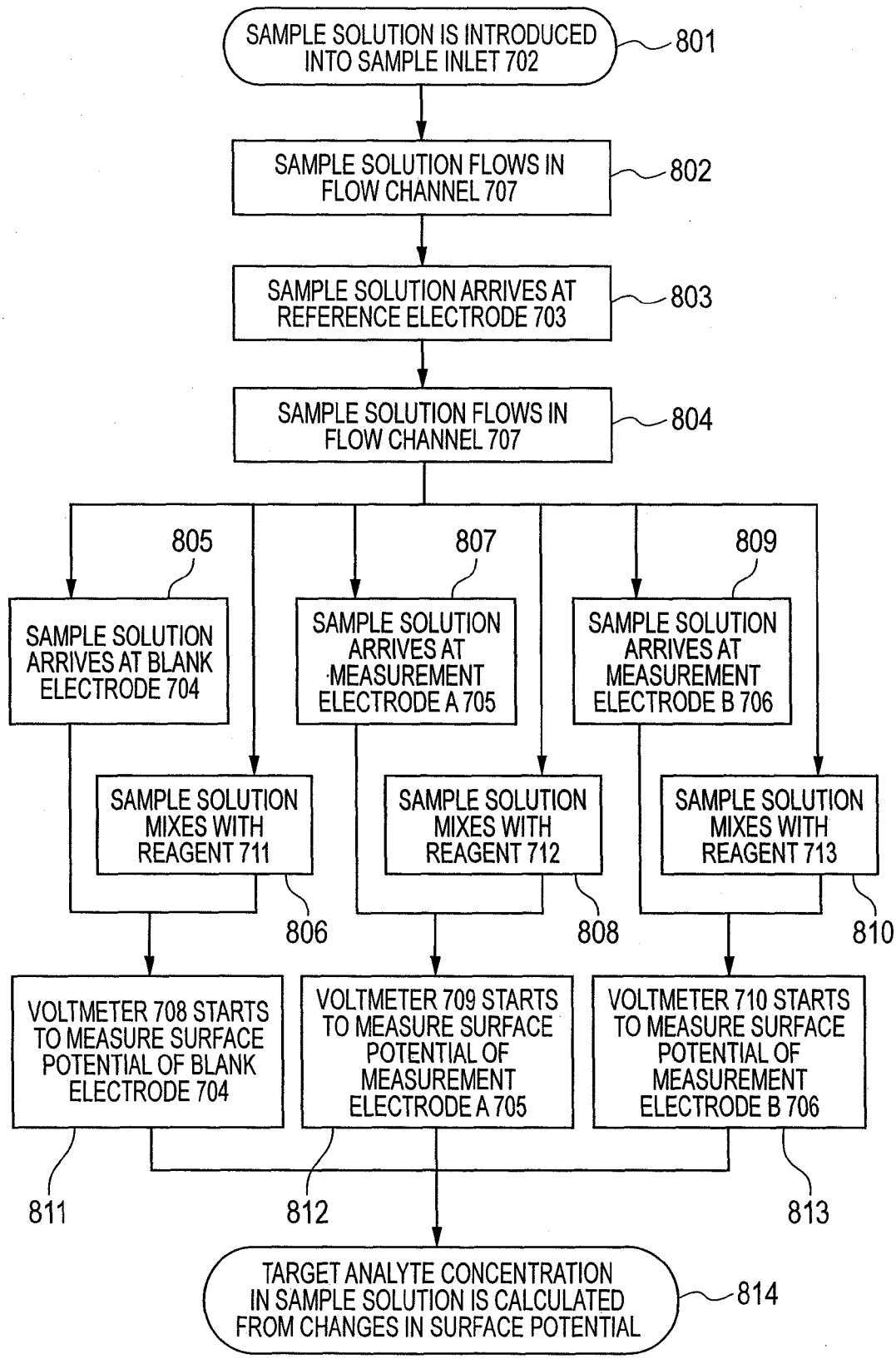
FIG. 8 is a view showing an example of a measurement flow using a potentiometric enzyme sensor chip according to the present invention.

Referring to the flowchart in FIG. 8, an example of measurement using the sensor chip shown in FIG. 7 is explained. First, a sample solution is introduced through the sample inlet 702 (801). The introduced sample solution flows in the flow channel 707 from top to bottom in the figure 802) and arrives at the reference electrode 703 (803). At this time, for the sample solution to flow, any kind of driving force may be used, whether it is a capillary force, pressure or gravity force. The sample solution further flows in the flow channel 707 (804) and arrives at the blank electrode 704, measurement electrode A 705 and measurement electrode B 706 through a branching point (805, 807, 809). Almost at the same time when the sample solution arrives at the blank electrode 704, it dissolves the reagent 711 for the blank electrode 704 or mixes with the reagent 711 (806) and chemical reaction starts. Also, almost at the same time when the sample solution arrives at the measurement electrode A 705 and measurement electrode B 706, it dissolves the reagents 712 and 713 for the measurement electrode A 705 and measurement electrode B 706 or mixes with the reagents 712 and 713 (808, 810) and chemical reaction starts. Therefore, the arrival of the sample solution at the blank electrode 704 is almost simultaneous with the reaction between the reagent for the blank electrode 704 and the sample solution, and the arrival of the sample solution at the measurement electrode A 705 and measurement electrode B 706 is almost simultaneous with the reaction between the reagents for the measurement electrode A 705 and measurement electrode B 706 and the sample solution. The changes in the surface potentials of the blank electrode 704, measurement electrode A 705 and measurement electrode B 706 as caused by these chemical reactions are measured by the voltmeter 708, voltmeter 709, and voltmeter 710 as changes in potential difference between the reference electrode 703 and blank electrode 704, between the reference electrode 703 and measurement electrode A 705, and between the reference electrode 703 and measurement electrode B 706 respectively (811, 812, 813). As in the case of FIG. 1, at the blank electrode 704, measurement electrode A 705, and measurement electrode B 706, when their respective chemical reactions start, it becomes possible to measure their respective surface potentials. Here, since the blank electrode 704, measurement electrode A 705 and measurement electrode B 706 are located in different branch flow channels, there does not exist the problem of crosstalk between the blank electrode and measurement electrodes which may arise in the sensor chip shown in FIG. 2. Also, in order to ensure that the sample solution spreads all over the surface of the reference electrode 703 before touching the blank electrode 704, measurement electrode A 705 and measurement electrode B 706, it is desirable that the distance between the reference electrode 703 and blank electrode 704, the distance between the reference electrode 703 and measurement electrode A 705 and the distance between the reference electrode 703 and measurement electrode B 706 be larger than the size of the reference electrode 703. The target analyte concentration in the sample solution is calculated using the measured changes in surface potential (814). In the method for calculating the target analyte concentration, it is also possible to employ a rate assay or fitting for the reaction process, taking advantage of being able to not only obtain the absolute values of surface potentials of the measurement electrodes and the surface potential difference between the measurement electrodes and blank electrode but also detect the start of reaction. Instead of the voltmeters 708, 709 and 710, field-effect transistors (FETs) may be used. The number of blank electrodes and the number of measurement electrodes may be further increased in the same way as in this example.

Figure 9:
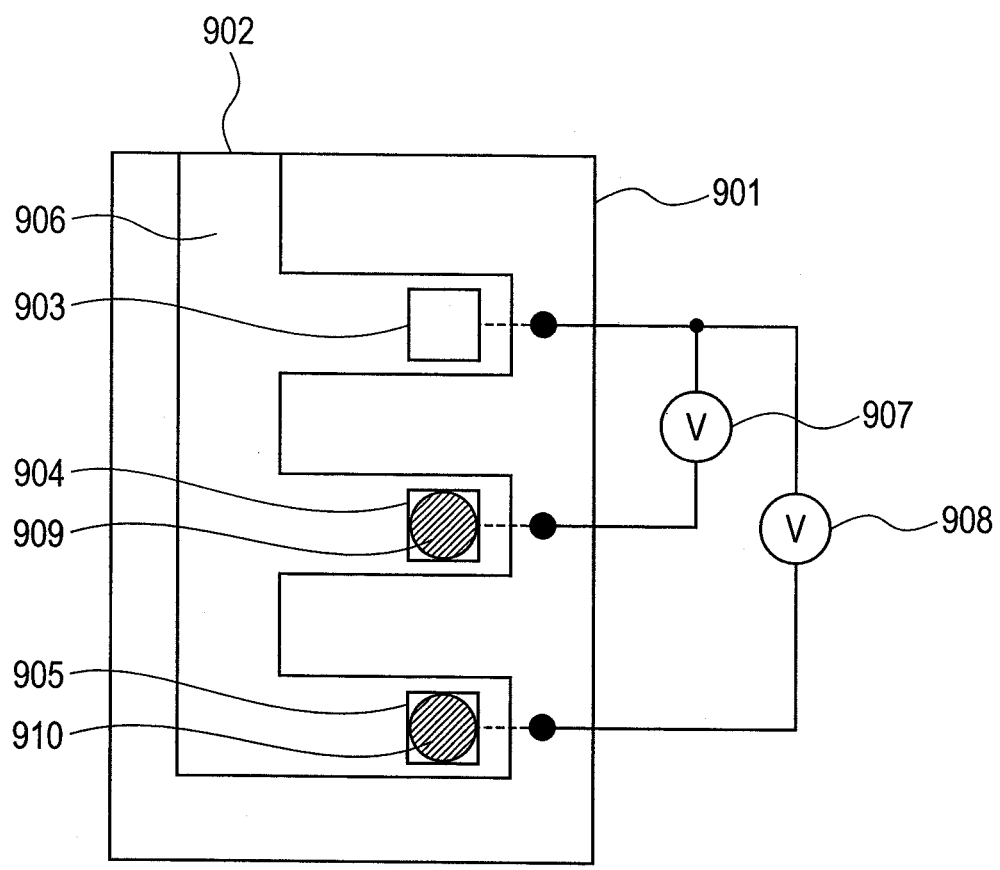
FIG. 9 is a view showing an example of a potentiometric enzyme sensor chip according to the present invention.

FIG. 9 shows an example of a potentiometric enzyme sensor chip according to the present invention. The chip has a substrate 901, a sample inlet 902, a reference electrode 903, a blank electrode 904, a measurement electrode 905, and a flow channel 906 and the reference electrode 903 and blank electrode 904 are connected to a voltmeter 907 and the reference electrode 903 and measurement electrode 905 are connected to a voltmeter 908. The flow channel 905 may be hollow or filled with filter paper or a carrier such as gels or beads. In that case, when necessary, a sheet is attached to the substrate in a way to cover the flow channel. A silver silver-chloride electrode or the like is used for the reference electrode 903. A noble metal such as gold, silver or platinum is used for the blank electrode 904 and measurement electrode 905. Preferably, an alkanethiol-modified gold electrode terminated with ferrocene such as 11-ferocenyl-1-undecanethiol is used. Reagents 909 and 910 are disposed over or around the blank electrode 904 and measurement electrode 905 or in the surrounding carrier. Preferably the reagents 909 and 910 are in a dry state. The reagent 909 for the blank electrode 904 does not contain some of the enzymes and catalysts as contained in the reagent 910 for the measurement electrode 905 or contains none of them. Therefore, the influence of potential variation of the reference electrode 903 or an interfering substance in the sample can be eliminated by comparison in surface potential between the blank electrode 904 and measurement electrode 905.

Figure 10:
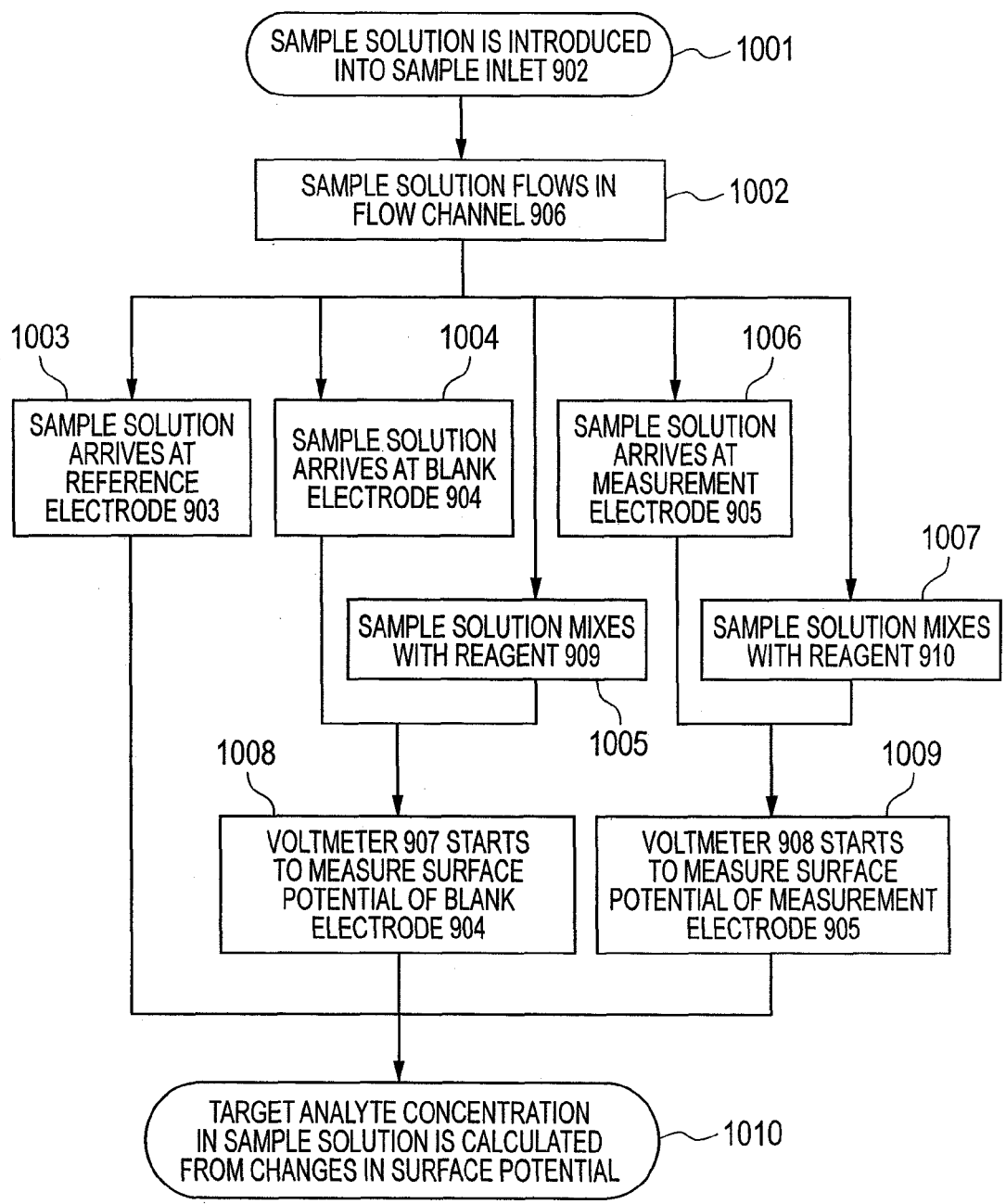
FIG. 10 is a view showing an example of a measurement flow using a potentiometric enzyme sensor chip according to the present invention.

Referring to the flowchart in FIG. 10, an example of measurement using the sensor chip shown in FIG. 9 is explained. First, a sample solution is introduced through the sample inlet 902 (1001). The introduced sample solution flows in the flow channel 906 from top to bottom in the figure and arrives at the electrodes through the respective branching points (1003, 1004, 1006). At this time, for the sample solution to flow, any kind of driving force may be used, whether it is a capillary force, pressure or gravity force. According to the distance from the sample inlet 902, the sample solution arrives at the reference electrode 903, blank electrode 904, and measurement electrode 905 in the order of mention. In other words, the events occur in the order of 1003, 1004, and 1006. Almost at the same time when the sample solution arrives at the blank electrode 904, it dissolves the reagent 909 for the blank electrode 904 or mixes with the reagent 909 (1005) and chemical reaction starts. Also, almost at the same time when the sample solution arrives at the measurement electrode 905, it dissolves the reagent 910 for the measurement electrode 905 or mixes with the reagent 910 (1007) and chemical reaction starts. Therefore, the arrival of the sample solution at the blank electrode 904 is almost simultaneous with the reaction between the reagent 909 for the blank electrode 904 and the sample solution, and the arrival of the sample solution at the measurement electrode 905 is almost simultaneous with the reaction between the reagent 910 for the measurement electrode 905 and the sample solution. The changes in the surface potentials of the blank electrode 904 and measurement electrode 905 as caused by these chemical reactions are measured by the voltmeter 907 and voltmeter 908 as changes in potential difference between the reference electrode 903 and blank electrode 904 and between the reference electrode 903 and measurement electrode 905 respectively (1008, 1009).

Since the sample solution arrives at the reference electrode 903 among the electrodes earliest, at the blank electrode 904 and measurement electrode 905, when their respective chemical reactions start, it becomes possible to measure their respective surface potentials. Here, since the blank electrode 904 and measurement electrode 905 are located in different branch flow channels, there does not exist the problem of crosstalk between the blank electrode and measurement electrode which may arise in the sensor chip shown in FIG. 2. The target analyte concentration in the sample solution is calculated using the measured changes in surface potential (1010). In the method for calculating the target analyte concentration, it is also possible to employ a rate assay or fitting for the reaction process, taking advantage of being able to not only obtain the absolute value of surface potential of the measurement electrode and the surface potential difference between the measurement electrode and blank electrode but also detect the start of reaction. Instead of the voltmeters 907 and 908, field-effect transistors (FETs) may be used.

Figure 11:
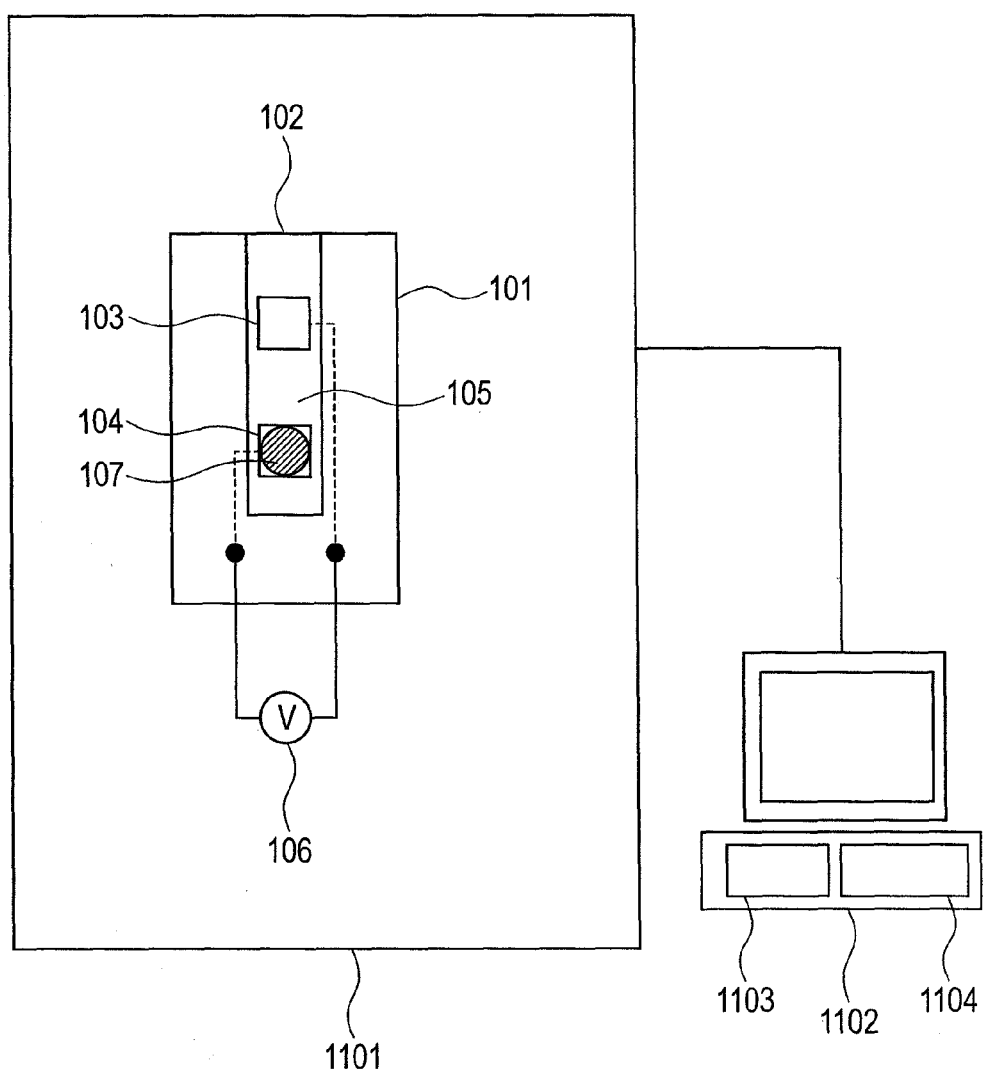
FIG. 11 is a block diagram showing an example of a measurement device using a potentiometric enzyme sensor chip according to the present invention.

FIG. 11 is a block diagram showing a measurement device which uses a potentiometric enzyme sensor chip according to the present invention. A measurement unit 1101 is the same as the potentiometric enzyme sensor chip shown in FIG. 1 and the measurement unit 1101 is connected to a data processing unit 1102. The data processing unit 1102 has a memory 1103 and a calculating unit 1104. The measurement unit 1101 may be another sensor chip according to the present invention. The data processing unit 1102 uses an analog-digital (AD) converter, etc to enable the measurement unit 1101 to measure potential differences. Before the sample solution is introduced, the flow channel 105 is dry, so the resistance between the reference electrode 103 and measurement electrode 104 is very large and the reading of the voltmeter 106 is not constant. As the sample solution is introduced here, the resistance between the reference electrode 103 and measurement electrode 104 decreases and the voltmeter comes to show a potential difference which depends on the chemical reaction to be measured. Therefore, before the sample solution arrives at the measurement electrode 104, the change in the potential difference measured by the voltmeter 106 is discontinuous and after its arrival, the change is no longer discontinuous. A discontinuous change in voltage potential difference can be detected, for example, by calculating the derivative or second derivative of change in potential difference with time. Also, since chemical reaction starts almost simultaneously with the arrival of the sample solution at the measurement electrode 104 as mentioned above, the arrival of the sample solution at the measurement electrode 104 as detected by the data processing unit 1102 is almost simultaneous with the start of chemical reaction, thereby making it possible to detect the start of chemical reaction. Although the potentiometric sensor chip shown in FIG. 1 is used in the example given here, even with another type of potentiometric sensor chip the arrival of the sample solution at the blank electrode and measurement electrode can be detected by the data processing unit 1102 similarly. Also, the data processing unit 1102 may be a personal computer, microcomputer or logic circuit and a numerical analysis method or analog differentiation circuit may be used for differentiation or secondary differentiation.

Figure 12:
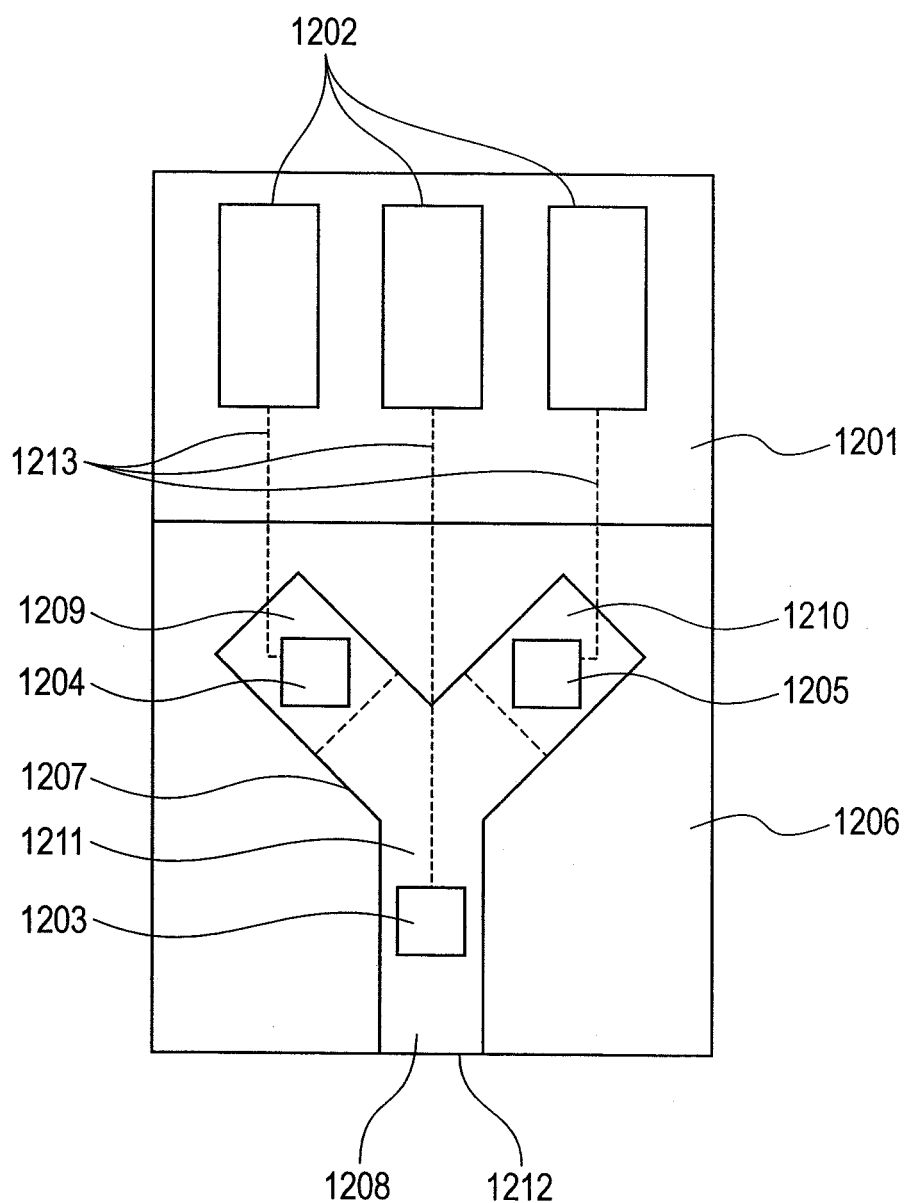
FIG. 12 is a view showing an example of a potentiometric enzyme sensor chip according to the present invention.
Figure 13:
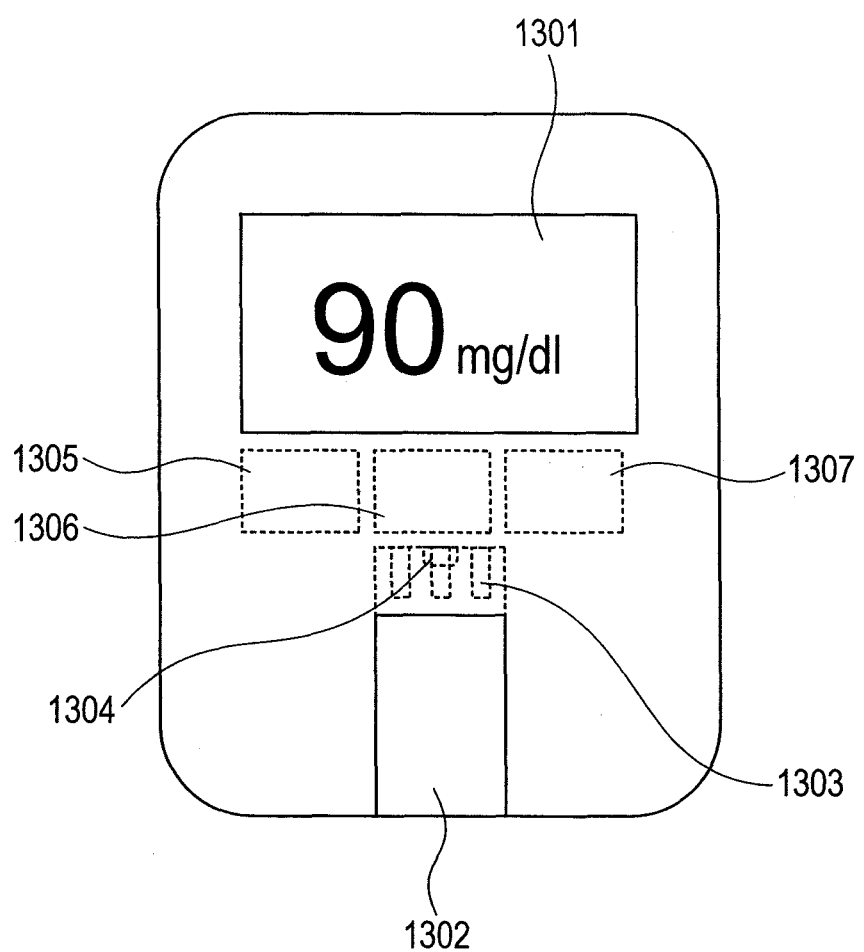
FIG. 13 is a view showing an example of a measurement device according to the present invention.

FIGS. 12 and 13 show an example of a potentiometric enzyme sensor chip according to the present invention and a measurement device therefor. The potentiometric sensor chip has a flow channel 1207 which branches ahead of a reference electrode 1203 like the one in FIG. 5, in which a blank electrode 1204 and a measurement electrode 1205 are located in branch flow channels respectively. How the potentiometric enzyme sensor chip was produced is briefly summarized below. Using semiconductor manufacturing equipment, three terminals 1202, a reference electrode 1203, a blank electrode 1204, and a measurement electrode 1205 were formed on a silicon substrate 1201. Taking into consideration the adhesion property for the next step of forming a thin meal film, chrome was used as the material of the terminals 1202 and electrodes 1203, 1204 and 1205. The electrodes were electrically connected to the terminals 1202 through buried interconnect wires 1213 and the surface except the terminals 1202 and electrodes 1203, 1204 and 1205 was covered by a silicon nitride film. Then, a thin metal film with a thickness of 100 nm was formed on the electrodes 1203, 1204 and 1205 and terminals 1202 by sputtering. In order to modify the surfaces of the electrodes 1203, 1204 and 1205, the sensor chip was immersed one hour in an ethanol solution in which 11-ferocenyl-1-undecanethiol was dissolved with a concentration of 500 µmol/l and then it was cleaned with ethanol and deionized water, twice each time, and dried under a nitrogen atmosphere. In order to form a silver silver-chloride on the reference electrode 1203, silver silver-chloride paste is coated on the reference electrode 1203 and dried round the clock and further the organic solvent contained in the silver silver-chloride paste was removed in a vacuum. 0.2 mm-thick silicone rubber penetrating the flow channel 1207 was attached as part of a cell 1206 on the sensor chip thus produced. One end of the flow channel 1207 was made a sample inlet 1212. Filter paper 1209 over the blank electrode, filter paper 1210 over the measurement electrode, and filter paper 1211 for the sample inlet were placed in the flow channel 1207. The filter paper thickness was 0.2 mm and when the filter paper 1209 over the blank electrode, filter paper 1210 over the measurement electrode and filter paper 1211 for the sample inlet are combined, they make up a shape corresponding to the shape of the flow channel 1207. The filter paper 1209 over the blank electrode and the filter paper 1210 over the measurement electrode were prepared by shaping filter paper into their respective shapes, dropping 1 µL of reagent for the blank electrode and 1 µL of reagent for the measurement electrode respectively and drying in a nitrogen atmosphere. The reagent for the blank electrode is composed of 299 µmol/l potassium ferricyanide, 1 µmol/l potassium ferrocyanide, and 0.1 M potassium phosphate (pH 7), and the reagent for the measurement electrode is composed of 299 µmol/l potassium ferricyanide, 1 µmol/l potassium ferrocyanide, 20 mg/ml glucose dehydrogenase, and 0.1 M potassium phosphate (pH 7). After the filter papers were placed in the flow channel 1207, 0.2 mm-thick silicone rubber was laid over them to complete the cell 1206 and sensor chip. The measurement device has a display unit 1301, a chip slot 1302, a memory 1305, a calculating unit 1306, and a voltmeter 1307. The voltmeter 1307 is connected to terminals 1303 and readings of the voltmeter 1308 are stored in the memory 1305.

Figure 14:
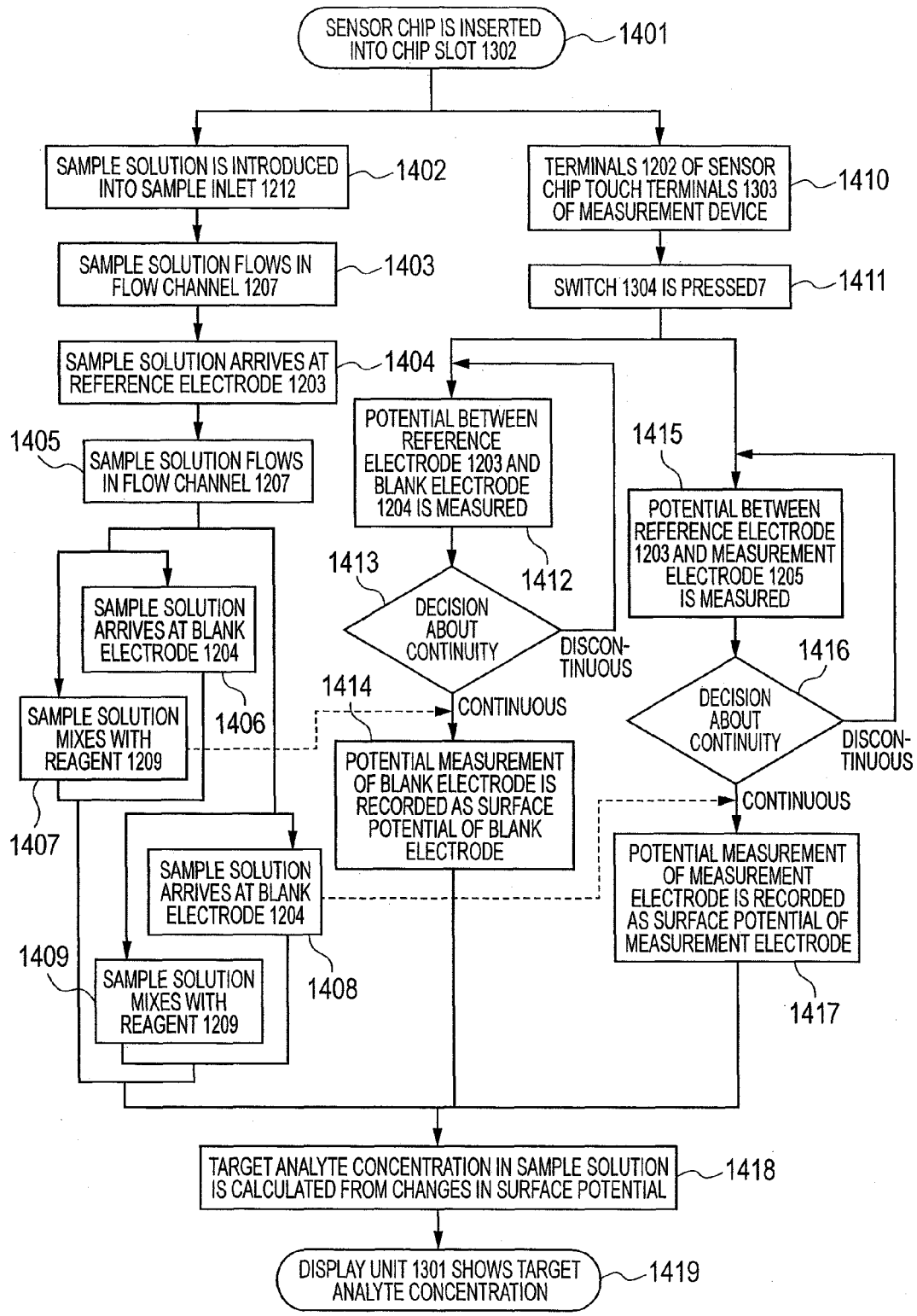
FIG. 14 is a view showing an example of a measurement flow using a potentiometric enzyme sensor chip according to the present invention.

Referring to the flowchart in FIG. 14, an example of measurement using the sensor chip and the measurement device therefor as shown in FIGS. 12 and 13 is explained below. First, the sensor chip is inserted into the chip slot 1302 (1401). The three terminals 1202 in the sensor chip touch the terminals 1303 in the measurement device (1410), so it becomes possible to measure the potential difference between the reference electrode 1203 and blank electrode 1204 and between the reference electrode 1203 and measurement electrode 1205 by the voltmeter 1307 in the measurement device. The insertion of the sensor chip is detected by a switch 1304 in the measurement device being pushed by the chip (1411). Consequently the measurement device starts to measure the potential difference between the electrodes (1412, 1415). As the blood serum of the sample solution is made to touch the sample inlet 1212, the sample solution is sucked into the flow channel due to a capillary phenomenon of the filter paper (1402). The sucked sample solution flows in the flow channel 1207 (1403) and first arrives at the reference electrode 1203 (1404), arrives at the branching point of the flow channel and arrives at the blank electrode 1204 and measurement electrode 1205 respectively (1406, 1408). When the solution arrives at the electrodes, the changes in potential difference between the reference electrode and blank electrode and between the reference electrode and measurement electrode, which have been so far discontinuous, become continuous. Also, the sample solution, which has arrived at the blank electrode and measurement electrode, dissolves the reagents near the electrodes respectively (1407, 1409) and chemical reaction starts. On the other hand, the calculating unit monitors the continuity of potential change (1413, 1416). When it detects transition from a discontinuous potential change to a continuous change, it starts to record the potential being measured, as the surface potential of the electrode (1414, 1417). A decision about the arrival of the sample solution at each electrode can be made not only based on continuity but also in reference to whether the absolute voltage value is adequate or not. Consequently, the surface potential of each electrode can be measured from when chemical reaction starts. The target analyte concentration in the sample solution is calculated from the obtained surface potential (1418) and shown on the display unit 1301 (1419).

Figure 16:
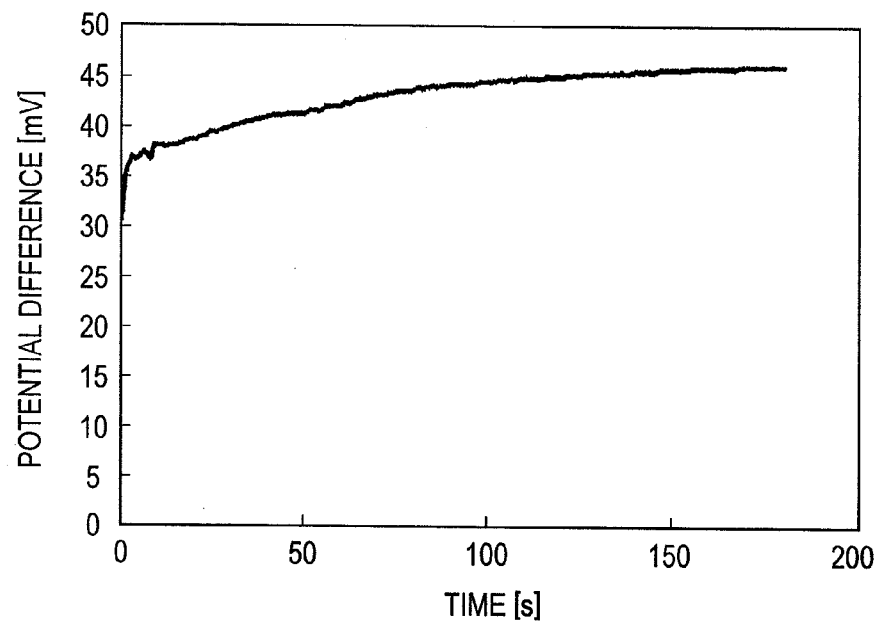
FIG. 16 is a view showing the result of processing of data obtained using a potentiometric enzyme sensor chip and a measurement device according to the present invention by a data processing method according to the present invention.
Figure 17:
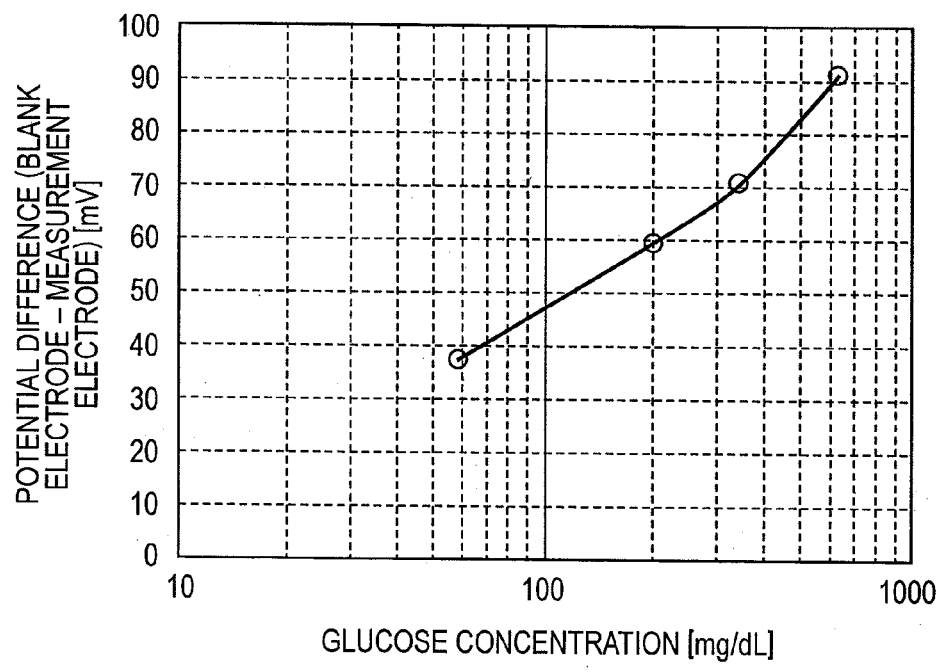
FIG. 17 is a view showing a calibration curve obtained using a potentiometric enzyme sensor chip and a measurement device according to the present invention.

The data obtained using the potentiometric enzyme sensor chip shown in FIG. 12 and the measurement device shown in FIG. 13 and the processing results of the data are shown in FIGS. 15(*a*) and (*b*) and FIG. 16. Also a previously obtained calibration curve is shown in FIG. 17. FIG. 15(*a*) shows a plot in which the horizontal axis represents time from the insertion of the sensor chip and the vertical axis represents potential difference with respect to the reference electrode and FIG. 15(*b*) shows a plot in which the horizontal axis is the same as in FIG. 15(*a*) and the vertical axis represents the second time derivative of potential difference with respect to the reference electrode. The graph shows that around 10 seconds, the potential difference changes from a level outside the graph to 200 mV or so. This is because the sample solution introduced through the sample inlet arrived at the blank electrode and measurement electrode. Here, in terms of second derivative, the value which had drastically changed converged to around 0. Before the arrival of the solution at the electrodes, the resistances between the reference electrode and blank electrode and between the reference electrode and measurement electrode were 100 MΩ or more. For that reason, due to external noise or noise from the measurement device itself, the reading of the voltmeter largely changed and the secondary differentiation was a value far from 0. As the solution arrived at the electrodes, the resistances between the reference electrode and blank electrode and between the reference electrode and measurement electrode decreased to 1 MΩ or so and the external noise component considerably decreased. Thus, the secondary differentiation value became near 0 and the potential difference also converged to 200 mV or so, a normally observed level. Here, FIG. 16 shows a plot of the potential difference between the blank electrode and measurement electrode where the measurement start point was the first point at which the absolute secondary differentiation value became 10 mV/s$^2$ or less. From the data thus obtained, 46.2 mV as the potential difference between the blank electrode and measurement electrode 180 seconds after the start of measurement was obtained. Using the previously obtained calibration curve (FIG. 17), this is found to correspond to a glucose concentration of 99 mg/dL.

If the start of reaction is not detected by the above method, it is necessary to put restrictions, such as having the user push the button manually after introducing the sample or introducing the sample within 10 seconds after setting up the sensor chip. If a method which relies on the user like this is adopted, an error may occur in the start time of measurement, leading to a measurement value error. Regarding the data in FIG. 16, a lag of 30 seconds in the detection of the start time of measurement causes an error equivalent to a glucose concentration of 2%. When the above method is adopted to detect the start of reaction, the error in the detection of the start time of measurement is very small. Since the data interval is 1 second, assuming an error of ±1 second, the error in the detection of the start time of measurement is 2 seconds and in this case, the error is 0.2% for the data in FIG. 16. As mentioned above, by detecting the reaction start time by the above method, the measurement error can be reduced. If the reaction start time is not detected, the measurement error can be reduced by lengthening the measurement time, for example, changing the reaction end point from 180 seconds after the start of measurement to 300 seconds after the start of measurement; however, a longer measurement time is unbeneficial for the user and also even if the measurement time is lengthened, the measurement error is smaller when the reaction start time is detected.

Figure 18:
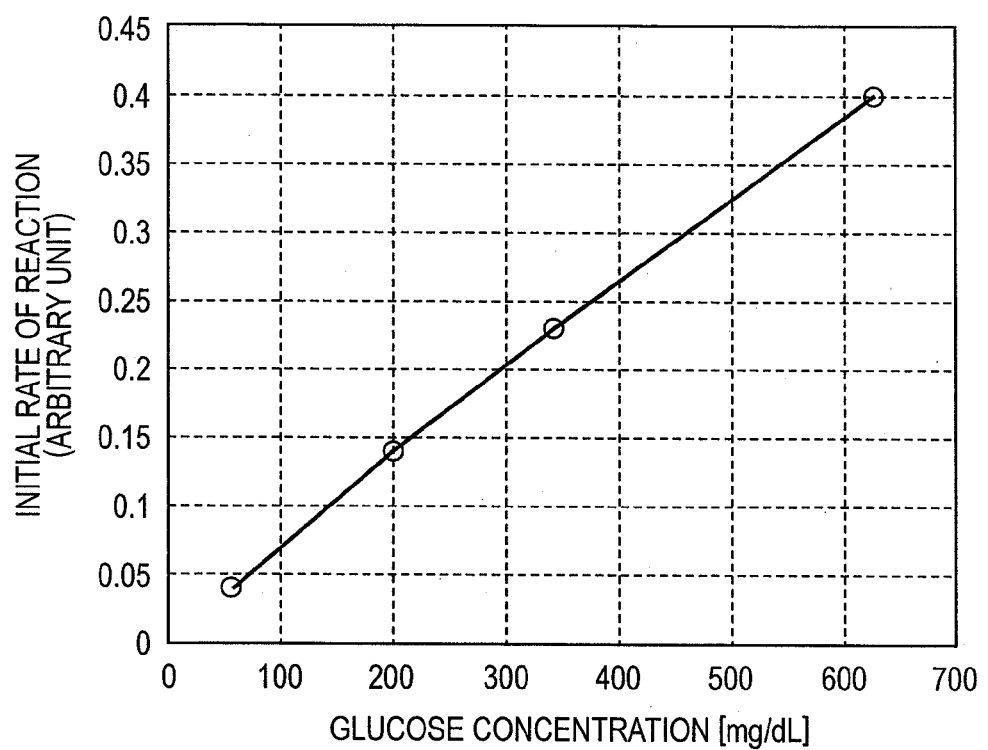
FIG. 18 is a view showing a calibration curve obtained using a potentiometric enzyme sensor chip and a measurement device according to the present invention.

FIG. 18 shows the calibration curve obtained by a rate assay. The horizontal axis represents the glucose concentration measured by the absorptiometric method and the vertical axis represents the initial rate of reaction. The rate of reaction v is calculated by the equation below from the difference E as potential difference, based on that the potential follows the Nernst Equation $$v = \frac{d}{dI}\left(\frac{RT}{F}\ln E\right) \qquad \text{[Equation 2]}$$

and an average of reaction rates in 5 to 10 seconds after the start of reaction was taken as the initial rate of reaction. When the initial rate of reaction was calculated similarly from the data in FIG. 16 and the calibration curve in FIG. 18 was used, the glucose concentration was found to be 106 mg/dL.

Although a difference of about 7% was observed in the result of measurement between the rate assay and the end point method, this difference is considered to be an error caused by the fact that the measurement time in the rate assay was shorter than in the end point method and it does not imply an intrinsic difference between the measurement methods.

DESCRIPTION OF REFERENCE NUMERALS

101,301,501,701,901 . . . Substrate
102,302,502,702,902,1208 . . . Sample inlet
103,303,503,703,903,1203 . . . Reference electrode
304,504,704,904,1204 . . . Blank electrode
104,305,505,905,1205 . . . Measurement electrode
705 . . . Measurement electrode A
706 . . . Measurement electrode B
105,306,506, 707,1207 . . . Flow channel
106,307,308,507,508,708,709,710,907,908,1307 . . . Voltmeter
107,309,310,509,510,711,712,713,909,910 . . . Reagent
1101 . . . Measurement unit
1102 . . . Data processing unit
1103,1305 . . . Memory
1104,1306 . . . Calculating unit 1201 . . . Silicon substrate
1202,1303 . . . Terminal
1206 . . . Cell
1209,1210,1211 . . . Filter paper
1301 . . . Display unit
1302 . . . Chip slot
1304 . . . Switch

The invention claimed is:

1. A sensor chip comprising:
a sample inlet that introduces a sample;
a reference electrode that the sample is made to touch;
a measurement electrode that has a measuring reagent and is made to touch the sample for measurement of a potential difference from the reference electrode; and
a blank electrode which has a reagent not containing part of the measuring reagent of the measurement electrode or containing none thereof and is made to touch the introduced sample for measurement of a potential difference from the reference electrode;
wherein the reference electrode and the measurement electrode are disposed so as for the introduced sample to arrive at the reference electrode earlier than at the measurement electrode.

2. The sensor chip as described in claim 1, wherein the blank electrode is located between the reference electrode and the measurement electrode.

3. The sensor chip as described in claim 1, further comprising:
a first flow channel branching from the flow channel stretching from the sample inlet in which the measurement electrode is located; and
a second flow channel branching from the flow channel stretching from the sample inlet in which the blank electrode is located.

4. The sensor chip as described in claim 1,
wherein the measurement electrode includes a plurality of measurement electrodes having different measuring reagents; and
wherein different flow channels branching from the flow channel stretching from the sample inlet are provided for the respective measurement electrodes.

5. A sensor chip comprising:
a sample inlet that introduces a sample;
a reference electrode that the sample is made to touch;
a measurement electrode that has a measuring reagent and is made to touch the sample for measurement of a potential difference from the reference electrode;
a first flow channel branching from the flow channel stretching from the sample inlet in which the reference electrode is located; and
a second flow channel branching from the flow channel stretching from the sample inlet in which the measurement electrode is located;
wherein the reference electrode and the measurement electrode are disposed so as for the introduced sample to arrive at the reference electrode earlier than at the measurement electrode.

6. A potentiometric assay method which uses a sensor chip including a reference electrode and a measurement electrode having a measuring reagent to react with an introduced sample, to measure a potential difference between the reference electrode and the measurement electrode, comprising the steps of:
introducing the sample;
making the sample touch the reference electrode;
after making the sample touch the reference electrode, making the sample touch the measurement electrode;
detecting time of transition in the potential difference from a discontinuous change to a continuous change; and
calculating a concentration of the sample from the change in the potential difference since the detected time using previously prepared data on relationship between potential differences and concentrations of the sample.

7. The potentiometric assay method as described in claim 6, wherein the discontinuous change and the continuous change are detected by differentiation or secondary differentiation of the change in the potential difference with time.

8. The potentiometric assay method as described in claim 6, wherein after the sensor chip is attached to a measurement device, the sample is introduced and after the sample concentration is calculated, the concentration is displayed on the measurement device.

9. An assay kit comprising:
a sensor chip that makes a sample touch; and
a measurement device to which the sensor chip is attached to measure a concentration of the sample,
the sensor chip including:
a sample inlet;
a reference electrode that the sample is made to touch;
a measurement electrode that has a measuring reagent and is made to touch the sample; and
a first terminal for measurement of potentials of the reference electrode and the measurement electrode,
wherein the reference electrode and the measurement electrode are disposed so as for the introduced sample to arrive at the reference electrode earlier than at the measurement electrode,
the measurement device including:
a slot for the sensor chip;
a second terminal that detects a voltage from the first terminal;
a memory storing data on relationship between potentials and concentrations of the sample;
a calculating unit that measures the voltage detected by the second terminal, detects time of a discontinuous change in potential difference between the reference electrode and the measurement electrode and calculates a concentration of the sample from the change in potential difference since the detected time; and
a display unit that displays the concentration calculated by the calculating unit.

10. The assay kit as described in claim 9,
wherein the measurement device includes an attachment detecting part for detecting attachment of the sensor chip; and
wherein the calculating unit starts to measure a potential upon detection of attachment by the attachment detecting part.

* * * * *